(12) United States Patent
Ivashchenko et al.

(10) Patent No.: US 8,329,689 B2
(45) Date of Patent: Dec. 11, 2012

(54) SUBSTITUTED INDOLES AND A METHOD FOR THE PRODUCTION AND USE THEREOF

(75) Inventors: Andrey Alexandrovich Ivashchenko, Moscow (RU); Sergey Yevgenievich Tkachenko, San Diego, CA (US); Alexander Viktorovich Khvat, San Diego, CA (US); Oleg Dmitrievich Mitkin, Khimki (RU); Ilya Matusovich Okun, San Diego, CA (US); Alexandr Sergeevich Kyselvev, San Diego, CA (US); Volodymyr Mikhailovich Kysil, Kiev (UA); Nikolay Filippovich Savchuk, Rancho Santa Fe, CA (US); Alexander Vasilievich Ivachtchenko, Encinitas, CA (US)

(73) Assignees: Alexandre Vasilievich Ivachtchenko, Encinitas, CA (US); Andrey Alexandrovich Ivashchenko, Moscow (RU); Nikolay Filippovich Savchuk, Rancho Santa Fe, CA (US)

( * ) Notice: Subject to any disclaimer, the term of this patent is extended or adjusted under 35 U.S.C. 154(b) by 408 days.

(21) Appl. No.: 12/600,251

(22) PCT Filed: May 17, 2007

(86) PCT No.: PCT/RU2007/000244
§ 371 (c)(1),
(2), (4) Date: Apr. 29, 2010

(87) PCT Pub. No.: WO2007/136300
PCT Pub. Date: Nov. 29, 2007

(65) Prior Publication Data
US 2011/0160197 A1    Jun. 30, 2011

(30) Foreign Application Priority Data

May 23, 2006   (RU) .............................. 2006-117557
May 23, 2006   (RU) .............................. 2006-117558

(51) Int. Cl.
*A61K 31/404*   (2006.01)
*A61K 31/407*   (2006.01)
*C07D 209/12*   (2006.01)
*C07D 498/04*   (2006.01)

(52) U.S. Cl. ..................... 514/229.8; 514/419; 544/101; 548/492

(58) Field of Classification Search ............... 514/229.8, 514/419; 544/101; 548/492
See application file for complete search history.

(56) References Cited

U.S. PATENT DOCUMENTS
5,198,552 A    3/1993   Trofimov et al.

FOREIGN PATENT DOCUMENTS

| CN | 1482118 | 3/2004 |
|---|---|---|
| CN | 1660807 | 8/2005 |
| DE | 2408603 | 9/1974 |
| DE | 2462471 | 5/1977 |
| EP | 1731506 A1 | 12/2006 |
| GB | 1417381 | 12/1975 |
| JP | 63-188665 | 8/1988 |
| WO | WO 90/08135 | 7/1990 |
| WO | WO 00/42045 A3 | 7/2000 |
| WO | WO 2004/060873 | 7/2004 |
| WO | WO 2005/087729 A1 | 9/2005 |
| WO | WO 2007/136300 | 11/2007 |

OTHER PUBLICATIONS

Tawara, et al. (Document No. 110:94995, CAPLUS) entered in STN Mar. 17, 1989.*
Grinev, et al. (Document No. 107:39560, CAPLUS) entered in STN Aug. 8, 1987.*
Kurilo, et al. (Document No. 90:137616, CAPLUS) entered in STN May 12, 1984.*

(Continued)

*Primary Examiner* — Shawquia Young
(74) *Attorney, Agent, or Firm* — Sughrue Mion, PLLC

(57) ABSTRACT

The invention relates to novel substituted indoles, to the use thereof in the form of pharmacological composition substances and to use of said composition for producing medicinal preparations used for preventing and treating viral diseases, in particular caused by viruses of infectious hepatitis (HCV, HBV), human immune deficiency (HIV), atypical pneumonia (SARS) and bird flu. The invention proposes novel substituted indoles of general formula (1) or the racemates or the optical isomers or the pharmaceutically acceptable salts and/or hydrates thereof, wherein $R^1$, $R_1^4$ and $R_2^4$ independently of each other are an aminogroup substituent selected for hydrogen, optionally substituted alkyl, optionally substituted cycloalkyl, optionally substituted aryl or optionally substituted heterocyclyl, or $R_1^4$ and $R_2^4$ together with a nitrogen atom, with which they are bound, form through $R_1^4$ and $R_2^4$ optionally substituted azaheterocyclyl or guanidyl; $R^2$ is analkyl substituent selected from hydrogen, an optionally substituted mercaptogroup, optionally substituted aminogroup and optionally substituted hydroxyl; $R^3$ is lower alkyl, $R^5$ is an hydrogen atom or $R^5$ together with an oxygen atom with which it is linked or $R_2^4$ together with a nitrogen atom with which it is linked close, via $R^5$ and $R_2^4$ an oxazine cycle; $R^6$ is a cyclic system substituent selected for hydrogen, a halogen atom, cyanogroup, optionally substituted aryl or substituted heterocyclyl.

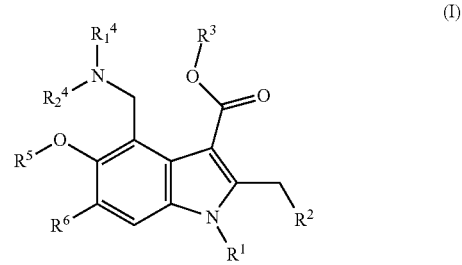

(I)

20 Claims, 3 Drawing Sheets

OTHER PUBLICATIONS

Figure 1:
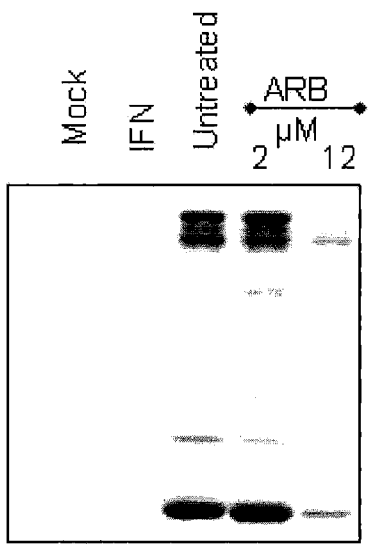

Fauran, et al. (Document No. 84:150615, CAPLUS) entered in STN May 12, 1984.*

Von Strandtmann, et al. (Document No. 81:49669, CAPLUS) entered in STN on May 12, 1984.*

Monti, et al. (Document No. 74:87740, CAPLUS) entered in STN on May 12, 1984.*

Grinev, et al. (Document No. 65: 56695, CAPLUS) entered in STN on Apr. 22, 2001.*

Vippagunta, et al. Advanced Drug Delivery Reviews 48 (2001) 3-26.*

HIV/AIDS [online] retrieved from the internet on Sep. 11, 2011 URL; (http://www.mayoclinic.com/health/hiv-aids/DS00005).*

SARS [online] retrieved from the internet on Sep. 11, 2011 URL; (http://www.emedicinehealth.com/script/main/art.asp?articlekey=137355).*

Augelli-Szafran, C.E. et al.: 'Identification and characterization of m4 selective antagonists' Bioorg. Med. Chem. Lett. vol. 8, No. 15, 1998, p. 1991.

Bartenschlager, Ralf; Pietschmann, Thomas . Proc Natl Acad Sci USA. vol. 102, No. 28, Jul. 12, 2005, pp. 9739-9740.

Berge S.M. et al.: 'Pharmaceutical Salts' J. Pharm. Sci. vol. 66, 1977, pp. 1-19.

Boriskin, Y.S. et al..: 'Arbidol: a broad-spectrum antiviral that inhibits acute and chronic HCV infection' Virology Journal vol. 3, 2006, p. 56 Retrieved from the Internet.

Brooks MJ: 'Studies with the antiviral drug arbidol' PHD Thesis 2003, pp. 1-2; 136-140.

Chai H. et al., Bioorg. Med. Chem., vol. 14, No. 4, 2006, pp. 911-917.

De Clercq E.: 'Recent highlights in the development of new antiviral drugs' Curr Opin Microbiol. vol. 8, No. 5, 2005, pp. 552-560.

Fedyakina Lt. et al.: 'Sensibility influenza viruses A/H5 recovered from wild birds on the territory of Russia to Arbidol in cell culture MDCK.' Virology Problem vol. 50, No. 6, 2005, pp. 32-35.

Glushkova, T.; Glushkov, R.: 'Arbidol—Interferon inductor, immunomodulator, antioxidant' Rev. Esp. Quimioter. vol. 13, 2000, (Suppl. 2) Abstract M182 [Abstract only in English].

Gluskhov, R. G.: 'Arbidol'. Drugs of the Future, 1992, 17(12): 1079-1081.

Gong Pin et al.: 'Preparation of new 5-hydroxy-1H-indole-3-carboxylic acid esters as antivirus agents for treating influenza', Database accession No. (142:355161).

Gong Ping Etal.: 'Preparation of 5-hydroxyindole-3-carboxylic acid ester derivative as antiviral agent for SARS', Database accession No. (145:62780).

Grinev A. N. et al. "Synthesis of alkylamine derivatives of 1-aryl-5-hydroxyindoles", Database accession No. (1966:456695) & Khimiya Geterotsiklicheskikh Soedinenii, 1966, N°3,pp. 395-397, [on-line] [Found in Internet ACS on STN], CA: 65: 10554c-f.

Grinev A..V.: 'Sintez i izuchenie antituberkuleznoi aktivnosti dialkialminoanoalkil-5-gidroksindol,, 5-gidroksibenzindol, 5-gridoksibenzofuran i 5-gidroksibenzofuran' Khimiko-Farmatsenticheskii Zhurnal vol. 4, No. 1, 1970, pp. 25-28.

Harriman Geraldine C. et al.: 'Preparation of pyrrolobenzopyranoquinolizine-carboxylates and analogs as CCR-5 chemokine receptor antagonists', Database accession No. (133:105029).

Hayden F.G.: 'Respiratory viral threats' Curr. Opin. Infect. Dis. vol. 19, No. 2, 2006, pp. 169-178.

Henter J.I et al.: 'Cytotoxic therapy for severe avian influenza A (H5N1) infection' Lancet. vol. 367, No. 9513, 2006, pp. 870-873.

Jain R. et al.: 'Limitations of current antiretroviral agents and opportunities for development' Curr. Pharm. Des. vol. 12, No. 9, 2006, pp. 1065-1074.

Lednicky J.A.; Rayner J.O.: 'Uncommon respiratory pathogens' Curr. Opin. Pulm. Med. vol. 12, No. 3, 2006, pp. 235-239.

Liu J.P.: 'Avian influenza—a pandemic waiting to happen?' J. Microbiol. Immunol. Infect. vol. 39, No. 1, 2006, pp. 4-10.

M.V. Mezentseva et al. Sintez, i protivovirusnaya aktivnost 2-fenoksi-metilnykh proizvodnykh 5-oksindola. Khimiko-farmatsevticheskii zhurnal 1991, 25 (5), 35-7 [Abstract only in English].

M.V. Mezentseva et al. Sintez, i protivovirusnaya aktivnost 2-fenoksi-metilnykh proizvodnykh 5-oksindola. Khimiko-farmatsevticheskii zhurnal, 1990, 10, 52-53 (compound XII-XV) [Abstract only in English].

Osnovnye lekarstvennye sredstva Meditsinskii Tsentr PRI Pravitelstve. Russian Federation, Moscow 1994, p. 30.

Song Y.-L. et al.: 'Synthesis of derivatives of N-alkyl-5-hydroxy-IH-indole-3-carboxylic ester hydrochloride', Database accession No. (142:134412) & Zhongguo Xinyao Zazhi vol. 13, No. 4, 2004, pp. 335-337.

Zhao C.-S. et al.: 'Synthesis and in-vitro anti-hepatitis B virus activities of several ethyl 5-hydroxy-1H-indole-3-carboxylates', Database accession No. (147:189029) & Chemical Research in Chinese University vol. 22, No. 5, 2006, pp. 577-583.

Zhong J Etal.: 'Robust hepatitis C virus infection in vitro' Proc Natl Acad Sci U S A vol. 102, 2005, pp. 9294-9299.

Zotova, S.A et al. Khim-Farm.ZH. vol. 29, No. 1, 1995, pp. 51-53.

\* cited by examiner

SUBSTITUTED INDOLES AND A METHOD FOR THE PRODUCTION AND USE THEREOF

CROSS REFERENCE TO RELATED APPLICATIONS

This application is a 35 USC §371 National Stage application of International Application No. PCT/RU2007/000244 filed May 17, 2007; which claims the benefit under 35 USC §119(a) to Russia Patent Application No. 2006117558 filed May 23, 2006 and to Russia Patent Application No. 2006117557 filed May 23, 2006. The disclosure of each of the prior applications is considered part of and is incorporated by reference in the disclosure of this application.

FIELD OF INVENTION

The present invention relates to the new substituted indoles and their application as active ingredients of pharmaceutical compositions, and utilization of the latter for preparation of customary formulation for treatment and prophylaxis of virus diseases, particularly caused by viruses of infectious hepatitis (HCV, HBV), human immunodeficiency virus (HIV), atypical pneumonia (SARS), and avian influenza.

BACKGROUND OF THE INVENTION

Virus infections may give rise to a great number of diseases that produces serious danger for health and existence of mankind. For the last 20 years no less than 30 brand-new infectious agents have been registered, such as: HIV, viral hepatitis, acute and chronic diarrhea, hemorrhagic fever (Ebola, Venezuelan, Brazilian, Rift valleys) [a] Lednicky J. A., Rayner J. O. Uncommon respiratory pathogens. Curr. Opin. Pulm. Med. 2006, 12(3), 235-239. b) Hayden F. G. Respiratory viral threats. Curr. Opin. Infect. Dis. 2006, 19(2), 169-178]. In particular, special anxiety is caused by the risk of infection by so named avian influenza. [a) Liu J. P. Avian influenza-a pandemic waiting to happen? J. Microbiol. Immunol. Infect. 2006, 39(1), 4-10. b) Henter J. I.; Chow C. B.; Leung C. W, Lau Y. L. Cytotoxic therapy for severe avian influenza A (H5N1) infection. Lancet. 2006 367(9513), 870-873. Review]. According to statistical data, 60-65% of epidemic infections have viral ethiology. Because of the complexity of interactions in triad "virus—host's organism—drug", most of modern antiviral drugs demonstrate side effects in the course of therapy and promote resistant virus strains [Jain R., Clark N. M., Diaz-Linares M., Grim S. A. Limitations of current antiretroviral agents and opportunities for development. Curr. Pharm. Des. 2006, 12(9), 1065-1074.]. At present, the number of antiviral drugs that could be used in clinical practice is extremely limited—only 43 low molecular weight substances [http://integrity.prous.com/integrity], that is far from satisfying requirements of prophylaxis and treatment of virus diseases. Moreover, there are considerable number of virus infections initiating all kind of diseases for treatment of which chemotherapeutic agents are absent. It is referred, for example, to the diseases caused by viruses of papilloma, adenoviruses, herpes-6, variola, syndrome SARS, hemorrhagic fevers, fever of the Western Nile, avian influenza [De Clercq E. Recent highlights in the development of new antiviral drugs. Curr Opin Microbiol. 2005, 8(5), 552-560].

Thus, the development of new antiviral drugs, particularly with new mechanism of antiviral action, high activity, and low toxicity is of great importance now.

There are known antiviral pharmaceutical compositions including as an active ingredient ethyl 6-bromo-4-[(dimethylamino)methyl]-5-hydroxy-1-methyl-2-(phenylthiomethyl)-1H-indole-3-carboxylate hydrochloride (Arbidol) [Arbidol, PCT Int. Appl. WO 9008135, 1990]

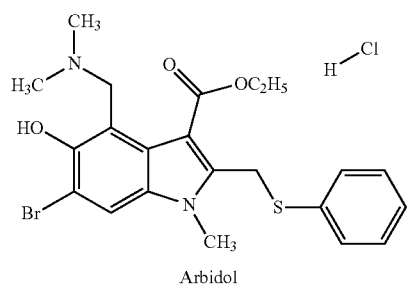

Arbidol

Arbidol is used for prophylaxis and treatment of diseases caused by viruses of influenza. It demonstrates the ability of inducing interferon and shows the immunomodulating effect. [Arbidol. Drugs R. D. 1999, September; 2(3), 171-172. Glushkova, T.; Glushkov, R. Arbidol—Interferon inductor, immunomodulator, antioxidant. Rev. Esp. Quimioter. 2000, 13(Suppl. 2), Abstr. M182]. Recently, antiviral activity of Arbidol against avian influenza viruses A/H5 was shown [Fedyakina I. T., Leneva I. A., Yamnikova S. S., Livov D. K., Glushkov R. G., Shuster A. M., Sensibility influenza viruses A/H5 recovered from wild birds on the territory of Russia to Arbidol in cell culture MDCK. Virology Problem, 2005, 50(6), 32-35], and Arbidol suppressing activity towards viruses of hepatitis C (HCV) was discovered as well [Y. S. Boriskin, E. I. Pécheur, S. J. Polyak. Arbidol: a broad-spectrum antiviral that inhibits acute and chronic HCV infection. Virology Journal 2006, 3:56 (http://www.virologyj.com/home)].

However, the main disadvantage of Arbidol is its high cellular toxicity ($CC_{50}$=10-20 mM) and, as a result of it, small therapeutic window or low selectivity index ($SI_{50}$). For example, for influenza virus it is equal only to 2.69 (on cellular line MDCK $TC_{50}$=62.5 μg/ml and $IC_{50}$=23.2 мкг/ml) [PCT Int Appl. WO 2005/087729 A1, 2005]. Its toxicity is even higher on some other cellular lines ($TC_{50}$=15-25 μg/ml) [Brooks M J: Studies with the antiviral drug arbidol [PhD thesis]. Melbourne, Australia: RMIT University; 2003].

There are known antiviral pharmaceutical compositions comprising as an active ingredient Arbidol analogs of the general formula A. [PCT Int Appl. WO 2004060873, 2004; PCT Int Appl. WO 2005/087729 A1, 2005. Bioorg. Med. Chem. 2006, 14(4), 911-917].

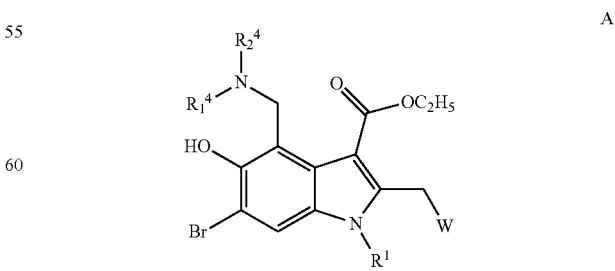

A wherein: $R^1$ is alkyl or cycloalkyl; $R_1^4$ and $R_2^4$ independently of each other are amino group substituents selected from hydrogen, optionally substituted alkyl, optionally substituted cycloalkyl, optionally substituted aryl or optionally substituted heterocyclyl, or $R_1^4$ and $R_2^4$ together with the N-atom they are attached to via $R_1^4$ and $R_2^4$ give rise to optionally substituted azaheterocyclyl; W is a substituted mercapto group.

Arbidol analogues of the general formula A also exhibit suppressing activity towards viruses of influenza A and B, as well as to viruses of hepatitis B (HBV) and human immunodeficiency virus (HIV) [Bioorg. Med. Chem. 2006, 14(4), 911-917. PCT Int Appl. WO 2005/087729 A1, 2005]. However, Arbidol analogues of the general formula A, as well as Arbidol itself, show high cellular toxicity and, as a result of it, low selectivity index. Thus, for example, selectivity index for this series of compounds towards hepatitis B is, as a rule, <10 ($SI_{50}$=1.81-10.8) [Bioorg. Med. Chem. 2006, 14(4), 911-917].

There are also known substituted indoles representing 1,2,3,7-tetrahydropyrrolo[3,2-f][1,3]benzoxazines exhibiting properties of selective M-4 muscarinic antagonists, potentially suitable for treatment of Parkinson disease [Augelli-Szafran, C. E.; Jaen, J. C.; Moreland, D. W.; Nelson, C. B.; Penvose-Yi, J. R.; Schwarz, R. D. Identification and characterization of m4 selective antagonists. *Bioorg. Med. Chem. Lett.* 1998, 8(15), 1991].

6-Methyl-1,2,3,7-tetrahydropyrrolo[3,2-f][1,3]benzoxazine-5-carboxylates B[DE 2408603, 1974; DE 2462471, 1977] also demonstrate various types of biological activity.

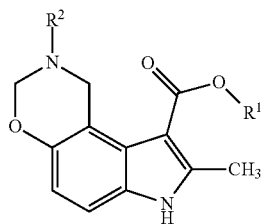

B

However, substituted 1,2,3,7-tetrahydropyrrolo[3,2-f][1,3]benzoxazines with antiviral activity have not been known yet.

Searching for highly effective antiviral drugs is now one of the main directions of the development of new pharmacological remedies for treatment of wide and diversified range of virus infections. For this reason working out of new compounds of this type, the pharmaceutical compositions including these compounds, and antiviral drug substances on their bases, methods for their preparation and application are of vital importance.

DISCLOSURE OF THE INVENTION

In the context of the present invention, the terms are generally defined as follows:

"Azaheterocycle" means aromatic or nonaromatic mono- or poly-cyclic system with, at least, one nitrogen atom in the cycle. Azaheterocycle may have one or more "cyclic system substituents".

"Aliphatic radical" means a radical derived at removal of hydrogen atom from nonaromatic C—H bond. Aliphatic radical may additionally contain any substituens—aliphatic or aromatic radicals, the meanings of which are defined in this section. The representatives of aliphatic radicals include alkyl, alkenyl, alkynyl, cycloalkyl, cycloalkenyl, heterocyclyl, heterocyclenyl, aralkenyl, aralkyloxyalkyl, aralkyloxycarbonylalkyl, aralkyl, aralkynyl, aralkyloxyalkenyl, heteroaralkenyl, heteroaralkyl, heteroaralkyloxyalkenyl, heteroaralkyloxyalkyl, annelated arylcycloalkyl, annelated heteroarylcycloalkyl, annelated arylcycloalkenyl, annelated heteroarylcycloalkenyl, annelated arylheterocyclyl, annelated heteroarylheterocyclyl, annelated arylheterocyclenyl, annelated heteroarylheterocyclenyl.

"Alkenyl" means aliphatic straight- or branched-hydrocarbon chain with 2-7 carbon atoms including C=C double bond. "Branched" means one or more lower alkyl substituents, such as methyl, ethyl or propyl, are attached to the straight alkenyl chain. Alkyl substituent may have one or more substituents such as: halogen, alkenyloxy, cycloalkyl, cyano; hydroxy, alkoxy, carboxy, alkynyloxy, aralkoxy, aryloxy, aryloxycarbonyl, alkylthio, heteroaralkyloxy, heterocyclyl, heterocyclylalkyloxy, alkoxycarbonyl, aralkoxycarbonyl, heteroaralkoxycarbonyl or $R_k^a R_{k+1}^a N-$, $R_k^a R_{k+1}^a NC(=O)-$, $R_k^a R_{k+1}^a NSO_2-$, where $R_k^a$ and $R_{k+1}^a$ independently of each other represent "amino group substituents", the meaning of which are defined in this section, for example, hydrogen, alkyl, aryl, aralkyl, heteroaralkyl, heterocyclyl or heteroaryl, or $R_k^a$ and $R_{k+1}^a$ together with the N-atom they are attached to, via $R_k^a$ and $R_{k+1}^a$ give rise to 4-7-membered heterocyclyl or heterocyclenyl. Methyl, trifluoromethyl, cyclopropylmethyl, cyclopentylmethyl, ethyl, n-propyl, iso-propyl, n-butyl, tert-butyl, n-pentyl, 3-pentyl, methoxyethyl, carboxymethyl, methoxycarbonylmethyl, benzyloxycarbonylmethyl, and pyridylmethyloxycarbonylmethyl are the preferred alkyl groups. Ethenyl, propenyl, n-butenyl, iso-butenyl, 3-methyl-buten-2-yl, n-pentenyl and cyclohexylbutenyl are the preferred alkenyl groups.

"Alkenyloxy" means alkenyl-O-group, in which alkenyl is defined in this section. Allyloxy and 3-butenyloxy are the preferred alkenyloxy groups.

"Alkenyloxyalkyl" means alkenyl-O-alkyl group, in which alkyl and alkenyl are defined in this section.

"Alkyl" means aliphatic hydrocarbon straight or branched chain with 1-12 carbon atoms. Branched means that the alkyl chain has one or more "lower alkyl" substituents. Alkyl group may have one or more substituents of the same or different structure ("alkyl substituent") including halogen, alkenyloxy, cycloalkyl, aryl, heteroaryl, heterocyclyl, aroyl, cyano, hydroxy, alkoxy, carboxy, alkynyloxy, aralkoxy, aryloxy, aryloxycarbonyl, alkylthio, heteroarylthio, aralkylthio, arylsulfonyl, alkylsulfonylheteroaralkyloxy, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, alkoxycarbonyl, aralkoxycarbonyl, heteroaralkyloxycarbonyl or $R_k^a R_{k+1}^a N-$, $R_k^a R_{k+1}^a NC(=O)-$, $R_k^a R_{k+1}^a NC(=S)-$, $R_k^a R_{k+1}^a NSO_2-$, where $R_k^a$ and $R_{k+1}^a$ independently of each other represent "amino group substituents", the meanings of which are defined in this section, for example, hydrogen, alkyl, aryl, aralkyl, heteroaralkyl, heterocyclyl or heteroaryl, or $R_k^a$ and $R_{k+1}^a$ together with the N-atom, they are attached to, via $R_k^a$ and $R_{k+1}^a$ give rise to 4-7-membered heterocyclyl or heterocyclenyl. Methyl, trifluoromethyl, cyclopropylmethyl, cyclopentylmethyl, ethyl, n-propyl, iso-propyl, n-butyl, tert-butyl, n-pentyl, 3-pentyl, methoxyethyl, carboxymethyl, methoxycarbonylmethyl, ethoxycarbonylmethyl, benzyloxycarbonylmethyl and pyridilmethyloxycarbonylmethyl are the preferred alkyl group. Cycloalkyl, aryl, heteroaryl, heterocyclyl, hydroxy, alkoxy, alkoxycarbonyl, aralkoxy, aryloxy, alkylthio, heteroarylthio, aralkylthio, alkylsulfonyl, arylsulfonyl, alkoxycarbonyl, aralkoxycarbonyl, heteroaralkyloxycarbonyl or $R_k{}^aR_{k+1}{}^aN$—, $R_k{}^aR_{k+1}{}^aNC$ (=O)—, annelated arylheterocyclenyl, annelated arylheterocyclyl are the preferred "alkyl substituents".

"Alkyloxyalkyl" means alkyl-O-alkyl group, in which alkyl groups are independent of each other and defined in this section. Methoxyethyl, ethoxymethyl, n-butoxymethyl, methoxypropyl and iso-propyloxyethyl are the preferred alkyloxyalkyl groups.

"Alkoxycarbonyl" means alkyl-O—C(=O)-group, in which alkyl is defined in this section. Methoxycarbonyl, ethoxycarbonyl, n-butoxycarbonyl, iso-propyloxycarbonyl, benzyloxycarbonyl and phenethyloxycarbonyl are the preferred alkoxycarbonyl groups.

"Alkylthio" means alkyl-S group, in which alkyl group is defined in this section.

"Alkoxy" means alkyl-O-group, in which alkyl is defined in this section. Methoxy, ethoxy, n-propoxy, iso-propoxy and n-butoxy are the preferred alkoxy groups.

"Alkoxycarbonylalkyl" means alkyl-O—C(=O)-alkyl-group, in which alkyl is defined in this section. Methoxycarbonylmethyl, ethoxy-carbonylmethyl, methoxy-carbonylethyl and ethoxy-carbonylethyl are the preferred alkoxycarbonylalkyl groups.

"Amino group" means $R_k{}^aR_{k+1}{}^aN$-group substituted or not by "amino group substituent", the meanings of $R_k{}^a$ and $R_{k+1}{}^a$ are defined in this section, for example, amino ($NH_2$), methylamino, diethylamino, pyrrolidino, morpholino, benzylamino or phenethylamino.

"Aminoacid" means natural or synthetic aminoacid, the meaning of which is defined in this section. Aminoacids containing α- or β-amino group are the preferred aminoacids. α-Aminoacids such as alanine, valine, leucine, isoleucine, proline, phenylalanine, triptophane, methionine, glycine, serine, threonine, and cysteine are natural aminoacids.

"Annelated cycle" (condensed cycle) means bi- or poly-cyclic system in which cycle, annelated cycle or polycycle together with the one it is annelated to, have, at least, two common atoms.

"Annelated arylheterocycloalkenyl" means annelated aryl and heterocycloalkenyl, the meanings of which are defined in this section. Annelated arylheterocycloalkenyl could be attached to any other fragment via any atom of its own system. Prefix "aza", "oxa" or "thia" before "heterocycloalkenyl" means that N, O or S atoms are introduced in the appropriate cyclic fragment, respectively. Annelated arylheterocycloalkenyl may have one or more "cyclic system substituens" of the same or different structure. N- and S-atoms belonging to heterocycloalkenyl fragment could be oxidized to N-oxide, S-oxide or S-dioxide. Indolinyl, 1H-2-oxoquinolinyl, 2H-1-oxoisoquinolinyl, 1,2-dihydroquinolinyl and others could be used as an annelated arylheterocycloalkenyl.

"Annelated arylheterocycloalkyl" means annelated aryl and heterocycloalkyl, the meanings of which are defined in this section. Annelated arylheterocycloalkyl could be attached to any other fragment via any atom of its own system. Prefix "aza", "oxa" or "thia" before "heterocycloalkyl" means that N, O or S atoms are introduced in the appropriate cyclic fragment, respectively. Annelated arylheterocycloalkyl may have one or more "cyclic system substituens" of the same or different structure. N- and S-atoms belonging to heterocyclyl fragment could be oxidized to N-oxide, S-oxide and S-dioxide. Indolyl, 1,2,3,4-tetrahydroisoquinolinyl, 1,3-benzodiocolyl and others could be used as an annelated arylheterocycloalkyl.

"Annelated arylcycloalkenyl" means annelated aryl and cycloalkenyl, the meanings of which are defined in this section. Annelated arylcycloalkenyl could be attached to any other fragment via any atom of its own system. Annelated arylcycloalkenyl may have one or more "cyclic system substituents" of the same or different structure. 1,2-Dihydronaphthalenyl, indenyl and others could be used as. annelated arylcycloalkenyl.

"Annelated arylcycloalkyl" means annelated aryl and cycloalkyl, the meanings of which are defined in this section. Annelated arylcycloalkyl could be attached to any other fragment via any atom of its own system. Annelated arylcycloalkyl may have one or more "cyclic system substituens" of the same or different structure. Indaninyl, 1,2,3,4-tetrahydranaphthyl, 5,6,7,8-tetrahydronapht-1-yl and others could be used as an annelated arylcycloalkyl.

"Annelated heteroarylcycloalkenyl" means annelated heteroaryl and cycloalkenyl, the meanings of which are defined in this section. Annelated heteroarylcycloalkenyl could be attached to any other fragment via any atom of its own system. Prefix "aza", "oxa" or "thia" before "heteroaryl" means that N, O or S atoms are introduced in the cyclic system, respectively. Annelated heteroarylcycloalkenyl may have one or more "cyclic system substituents" of the same or different structure. N-Atom belonging to the heteroaryl ring could be oxidized to N-oxide. 5,6-dihydroquinolinyl, 5,6-dihydroisoquinolinyl, 4,5-dihydro-1H-benzimidazolyl are the representatives of annelated heteroarylcycloalkenyl.

"Annelated heteroarylcyckloalkyl" means annelated heteroaryl and cycloalkyl the meanings of which are defined in this section. Annelated heteroarylcycloalkyl could be attached to any other fragment via any atom of its own system. Prefix "aza", "oxa" or "thia" before "heteroaryl" means that N, O or S atoms are introduced in the appropriate cyclic fragment, respectively. Annelated heteroarylcycloalkyl may have one or more "cyclic system substituents" of the same or different structure. N-Atom of the heteroaryl part of the molecule could be oxidized to N-oxide. 5,6,7,8-Tetrahydroquinolinyl, 5,6,7,8-tetrahydroisoquinolinyl, 4,5,6,7-tetrahydro-1H-benzimidazolyl and others could be used as an annelated heteroarylcycloalkyles.

"Annelated heteroarylhetrocyclenyl" means annelated heteroaryl and heterocyclenyl, the meanings of which are defined in this section. Annelated heteroarylheterocyclenyl could be attached to any other fragment via any atom of its own system. Prefix "aza", "oxa" or "thia" before "heteroaryl" means that N, O or S atoms are introduced in the appropriate cyclic fragment, respectively. Annelated heteroarylheterocyclenyl may have one or more "cyclic system substituents" of the same or different structure. N-Atom of heteroaryl fragment could be oxidized to N-oxide. N- And S-atoms belonging to heterocyclenyl fragment could be oxidized to N-oxide, S-oxide and S-dioxide. 1,2-Dihydro[2,7]naphthiridinyl, 7,8-dihydro[1,7]naphthiridinyl, 6,7-dihydro-3H-imidazo[4,5-c]pyridyl and others could be used as an annelated heteroarylhetrocyclenyl.

"Annelated heteroarylheterocyclyl" means annelated heteroaryl and heterocyclyl, the meanings of which are defined in this section. Annelated heteroarylheterocyclyl could be attached to any other fragment via any atom of its own system. Prefix "aza", "oxa" or "thia" before "heteroaryl" means that N, O or S atoms are introduced in the appropriate cyclic fragment, respectively. Annelated heteroarylheterocyclyl may have one or more "cyclic system substituents" of the same or different structure. N-Atom belonging to heteroaryl fragment could be oxidized to N-oxide. N- And S-atoms of heterocyclyl fragment could be oxidized to N-oxide, S-oxide and S-dioxide. 2,3-Dihydro-1H-pyrrolo[3, 4-1)]quinolin-2-yl, 2,3-dihydro-1H-pyrrolo[3,4-b]indol-2-yl, 1,2,3,4-tetrahydro[1,5]naphthiridinyl and others could be used as an annelated heteroarylheterocyclyl.

"Aralkenyl" means aryl-alkenyl group, in, which the meanings of aryl and alkenyl are defined in this section. For example, 2-phenethenyl is aralkenyl group.

"Aralkyl" means alkyl group substituted by one or more aryl groups, in which the meanings of aryl and alkyl are defined in this section. For example, benzyl-, 2,2-diphenylethyl- or phenethyl- are aralkyl groups.

"Aralkylamino" means aryl-alkyl-NH-group, in which the meanings of aryl and alkyl are defined in this section.

"Aralkylsulfinyl" means aralkyl-SO-group, in which the meaning of aralkyl is defined in this section.

"Aralkylsulfonyl" means aralkyl-$SO_2$-group, in which the meaning of aralkyl is defined in this section.

"Aralkylthio" means aralkyl-S-group, in which the meaning of aralkyl is defined in this section.

"Aralkoxy" means aralkyl-O-group, in which the meaning of aralkyl is defined in this section. For example, benzyloxy or 1- or 2-naphthylenmethoxy are aralkyl groups.

"Aralkoxyalkyl" means aralkyl-O-alkyl-group, in which the meanings of aralkyl and alkyl are defined in this section. For example, benzyloxyethyl is aralkyl-O-alkyl group.

"Aralkoxycarbonyl" means aralkyl-O—C(=O)-group, in which the meaning of aralkyl is defined in this section. Benzyloxycarbonyl is an example of aralkoxycarbonyl group.

"Aralkoxycarbonylalkyl" means aralkyl-O—C(=O)-alkyl-group, in which the meanings of aralkyl and alkyl are defined in this section. Benzyloxycarbonylmethyl or benzyloxycarbonylethyl are examples of aralkoxycarbonylalkyl groups.

"Aryl" means aromatic mono- or polycyclic system with 6-14 carbon atoms, preferably 6-10 C-atoms. Aryl may have one or more "cyclic system substituents" of the same or different structure. Phenyl or naphthyl, substituted phenyl or substituted naphthyl are the representatives of aryl groups. Aryl could be annelated to nonaromatic cyclic system or heterocycle.

"Arylcarbamoyl" means aryl-NHC(=O)-group, in which the meaning of aryl is defined in this section.

"Aryloxy" means aryl-O-group, in which the meaning of aryl is defined in this section. Phenoxy- and 2-naphthyloxy- are the representatives of aryloxy group.

"Aryloxycarbonyl" means aryl-O—C(=O)-group, in which the meaning of aryl is defined in this section. Phenoxycarbonyl and 2-naphthoxycarbonyl are the representatives of aryloxycarbonyl groups.

"Arylsulfinyl" means aryl-SO-group, in which the meaning of aryl is defined in this section.

"Arylsulfonyl" means aryl-$SO_2$-group, in which the meaning of aryl is defined in this section.

"Arylthio" means aryl-S-group, in which the meaning of aryl is defined in this section. Phenylthio- and 2-naphthylthio- are the representatives of arylthio groups.

"Aroylamino" means aroyl-NH-group, in which the meaning of aroyl is defined in this section.

"Aroyl" means aryl-C(=O)-group, in which the meaning of aryl is defined in this section. Benzoyl-,1- and 2-naphthoyl- are the representatives of aroyl groups.

"Aromatic radical" means a radical derived at removal of hydrogen atom from aromatic C—H bond. "Aromatic" radical implies aryl and heteroaryl cycles, the meanings of which are defined in this section. Aryl and heteroaryl cycles may additionally contain substituents, such as aliphatic and aromatic radicals, the meanings of which are defined in this section. Aryl, annelated cycloalkenylaryl, annelated cycloalkylaryl, annelated heterocyclylaryl, annelated heterocyclenylaryl, heteroaryl, annelated cycloalkylheteroaryl, annelated cycloalkenylheteroaryl, annelated heterocyclenylheteroaryl and annelated heterocyclylheteroaryl are the representatives of aromatic radicals.

"Aromatic cycle" means a plane cyclic system, in which all atoms take part in the formation of common conjugation system comprising, according to Hückel rule, (4n+2) π-electrons (n is a whole nonnegative number). Benzene, naphthalene, anthracene and others are the representatives of aromatic cycles. In the case of "heteroaromatic cycles" π-electrons and p-electrons of heteroatoms participate in the conjugation, so that their total number is equal to (4n+2) as well. Pyridine, thiophene, pyrrole, furan, thiazole and others are the representatives of such cycles. Aromatic cycle may have one or more "cyclic system substituents" or could be annelated to nonaromatic cycle, heteroaromatic or heterocyclic system.

"Acyl" means H—C(=O)—, alkyl-C(=O)—, cycloalkyl-C(=O), heterocyclyl-C(=O)—, heterocyclylalkyl-C(=O)—, aryl-C(=O)—, arylalkyl-C(=O)—, heteroaryl-C(=O)—, heteroarylalkyl-C(=O)-groups, in which alkyl-, cycloalkyl-, heterocyclyl-, heterocyclylalkyl-, aryl-, arylalkyl-, heteroaryl-, heteroarylalkyl are defined in this section.

"Acylamino" means acyl-NH-group in which the meaning of acyl is defined in this section.

"1,2-vinyl radical" means —CH=CH-group with one or more "alkyl substituents" of the same or different structure, the meanings of which are defined in this section.

"Halogen" means fluorine, chlorine, bromine and iodine. Preference is given to fluorine, chlorine and bromine.

"Heteroannelated cycle" means that the cycle attached (annelated or condenced) to another cycle or polycycle contains, at least, one heteroatom.

"Heteroaralkenyl" means heteroaryl-alkenyl-group, in which the meanings of heteroaryl and alkenyl are defined in this section. Preferably, heteroarylalkenyl contains the lower alkenyl group. 4-Pyridylvinyl, thienylethenyl, imidazolylethenyl, pyrazinylethenyl are the representatives of heteroaralkenyl radical.

"Heteroaralkyl" means heteroaryl-alkyl-group, in which heteroaryl and alkyl are defined in this section. Pyridylmethyl, thienylmethyl, furylmethyl, imidazolylmethyl, pyrazinylmethyl are the representatives of heteroaralkyl radicals.

"Heteroaralkyloxy" means heteroarylalkyl-O-group, in which the meaning of heteroarylalkyl is defined in this section. 4-Pyridylmethyloxy, 2-thienylmethyloxy are the representatives of heteroaralkyloxy groups.

"Heteroaryl" means aromatic mono- or polycyclic system with 5-14 carbon atoms, preferably 5-10 C-atoms, in which one or more carbon atoms are substituted by one or more heteroatoms, such as N, S or O. Prefix "aza", "oxa" or"thia" before "heteroaryl" means that N, O or S atoms are introduced in the appropriate cyclic fragment, respectively. N-Atom of heteroaryl cycle could be oxidized to N-oxide. Heteroaryl may have one or more "cyclic system substituents" of the same or different structure. Pyrrolyl, furanyl, thienyl, pyridyl, pyrazinyl, pyrimidinyl, isooxazolyl; isothiazolyl, tetrazolyl, oxazolyl, thiazolyl, pyrazolyl, furazanyl, triazolyl, 1,2,4-thiadiazolyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothiazenyl, quinolinyl, imidazolyl, thienopyridyl, quinazolinyl, thienopyrimidinyl, pyrrolopyridinyl, imidazopyridinyl, isoquinolinyl, benzoazaindolyl, 1,2,4-triazinyl, thienopyrrolyl, furopyrrolyl and others are the representatives of heteroaryl radicals.

"Heteroarylsulfonylcarbamoyl" means heteroaryl-$SO_2$—NH—C(=O)-group, in which heteroaryl is defined in this section.

"Heteroaroyl"—means heteroaryl-C(=O)-group, in which the meaning of heteroaryl is defined in this section. Nicotinoyl, thienoyl, pyrazoloyl are the representatives of heteroaroyl groups.

"Heterocyclenyl" means nonaromatic mono- or polycyclic system including 3-13 C-atoms, preferably 5-13 C-atoms in which one or more carbon atoms are substituted by heteroatoms such as N, O or S and which contains, at least, one —C=C— or —C=N-double bond. Prefix "aza", "oxa" or "this" before "heterocyclenyl" means that N, O or S atoms are introduced in the appropriate cyclic fragment, respectively. Heterocyclenyl may have one or more "cyclic system substituens" of the same or different structure. N- And S-atoms belonging to heterocyclenyl fragment could be oxidized to N-oxide, S-oxide and S-dioxide. 1,2,3,4-Tetrahydropyridinyl, 1,2-dihydropyridinyl, 1,4-dihydropyridinyl, 2-pyrrolinyl, 3-pyrrolinyl, 2-imidazolyl, 2-pyrazolinyl, dihydrofuranyl, dihydrothiophenyl and others are examples of heterocyclenyl.

"Heterocyclyl" means aromatic or nonaromatic mono- or polycyclic system with 3-10 C-atoms, preferably 5-6 C-atoms in which one or more carbon atoms are substituted by heteroatom such as N, O or S. Prefix "aza", "oxa" or "this" before "heterocyclyl" means that N, O or S atoms are introduced in the appropriate cyclic fragment, respectively. Heterocyclyl may have one or more "cyclic system substituents" of the same or different structure. N- And S-atoms belonging to heterocyclic fragment could be oxidized to N-oxide, S-oxide and S-dioxide. Piperidinyl; pyrrolidinyl, piperazinyl, morpholinyl, thiomorpholinyl, thiazolidinyl, 1,4-dioxan-2-yl, tetrahydrofuranyl, tetrahydrothiophenyl and others are examples of heterocyclyl.

"Heterocyclyloxy" means heterocyclyl-O-group, in which heterocyclyl is defined in this section.

"Hydrate" means stoichiometric or nonstoichiometric compositions of the compounds or their salts with water.

"Hydroxyalkyl" means HO-alkyl-group, in which alkyl is defined in this section.

"Substituent" means a chemical radical attached to the scaffold (fragment), for example, "alkyl group substituent", "amino group substituent", "carbamoyl substituent", "cyclic system substituent", the meanings of which are defined in this section.

"Alkyl substituent" means a substituent attached to alkyl or alkenyl group, the meanings of which are defined in this section. It is selected from hydrogen, alkyl, halogen, alkenyloxy, cycloalkyl, aryl, heteroaryl, heterocyclyl, aroyl, cyano, hydroxy, alkoxy, carboxy, alkynyloxy, aralkoxy, aryloxy, aryloxycarbonyl, alkylthio, heteroarylthio, aralkylthio, arylsulfonyl, alkylsulfonylheteroaralkyloxy, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, alkoxycarbonyl, aralkoxycarbonyl, heteroaralkyloxycarbonyl or $R_k^a R_{k+1}^a N$—, $R_k^a R_{k+1}^a NC(=O)$—, $R_k^a R_{k+1}^a NSO_2$—, where $R_k^a$ and $R_{k+1}^a$ independently of each other represent "amino group substituent", the meanings of which are defined in this section, for example, hydrogen, alkyl, aryl, aralkyl, heteroaralkyl, heterocyclyl or heteroaryl, or $R_k^a$ and $R_{k+1}^a$ together with the N-atom, they are attached to, via $R_k^a$ and $R_{k+1}^a$ give rise to 4-7-membered heterocyclyl or heterocyclenyl. Methyl, trifluoromethyl, cyclopropylmethyl, cyclopentylmethyl, ethyl, n-propyl, iso-propyl, n-butyl, tert-butyl, n-pentyl, 3-pentyl, methoxyethyl, carboxymethyl, methoxycarbonylmethyl, ethoxycarbonylmethyl, benzyloxycarbonylmethyl, methoxycarbonylmethyl, and pyridylmethyloxycarbonylmethyl are the representatives of alkyl groups. Cycloalkyl, aryl, heteroaryl, heterocyclyl, hydroxy, alkoxy, alkoxycarbonyl, aralkoxy, aryloxy, alkylthio, heteroarylthio, aralkylthio, alkylsulfonyl, arylsulfonyl, alkoxycarbonyl, aralkoxycarbonyl, heteroaralkyloxycarbonyl or $R_k^a R_{k+1}^a N$—, $R_k^a R_{k+1}^a NC(=O)$—, annelated arylheterocyclenyl, annelated arylheterocyclyl are the preferred "alkyl substituents". The meanings of "alkyl group substituents" are defined in this section.

"Amino group substituent" means a substituent attached to amino group. Amino group substituent represents hydrogen, alkyl, cycloalkyl, aryl, heteroaryl, heterocyclyl, acyl, aroyl, alkylsulfonyl, arylsulfonyl, heteroarylsulfonyl, alkylaminocarbonyl, arylaminocarbonyl, heteroarylaminocarbonyl, heterocyclylaminocarbonyl, alkylaminothiocarbonyl, arylaminothiocarbonyl, heteroarylaminothiocarbonyl, heterocyclylaminothiocarbonyl, annelated hetero arylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, alkoxycarbonylalkyl, aralkoxycarbonylalkyl, heteroaralkyloxycarbonylalkyl. The meanings of "amino group substituents" are defined in this section.

"Carbamoyl substituent" means a substituent attached to carbamoyl group, the meaning of which is defined in this section. Carbamoyl substituent could be selected from hydrogen, alkyl, cyckloalkyl, aryl, heteroaryl, heterocyclyl, alkoxycarbonylalkyl, aralkoxycarbonylalkyl, heteroaralkyloxycarbonylalkyl or $R_k^a R_{k+1}^a N$—, $R_k^a R_{k+1}^a NC(=O)$-alkyl, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl. Alkyl, cycloalkyl, aryl, heteroaryl, heterocyclyl, alkoxycarbonylalkyl, aralkoxycarbonylalkyl, heteroaralkyloxycarbonylalkyl or $R_k^a R_{k+1}^a N$—; $R_k^a R_{k+1}^a NC(=O)$-alkyl, annelated arylheterocyclenyl, annelated arylheterocyclyl are the preferred "carbamoyl substituents". The meanings of "carbamoyl substituents" are defined in this section.

"Nucleophilic substituent" is a chemical radical attached to the scaffold as a result of a reaction with a nucleophilic reagent, for example, one selected from a group of primary or secondary amines, alcohols, phenols, mercaptans and thiophenols.

"Cyclic system substituent" means a substituent attached to an aromatic or nonaromatic cyclic system selected from hydrogen, alkyl, alkenyl, alkynyl, aryl, heteroaryl, aralkyl, heteroaralkyl, hydroxy, hydroxyalkyl, amino, aminoalkyl, alkoxy, aryloxy, acyl, aroyl, halogen, nitro, cyano, carboxy, alkoxycarbonyl, aryloxycarbonyl, aralkoxycarbonyl, alkyloxyalkyl, aryloxyalkyl, heterocyclyloxyalkyl, arylalkyloxyalkyl, heterocyclylalkyloxyalkyl, alkylsulfonyl, arylsulfonyl, heterocyclylsulfonyl, alkylfulfinyl, arylsulfinyl, heterocyclylsulfinyl, alkylthio, arylthio, heterocyclylthio, alkylsulfonylalkyl, arylsulfonylalkyl, heterocyclylsulfonylalkyl, alkylsulfinylalkyl, arylsulfinylalkyl, heterocyclylsulfinylalkyl, alkylthioalkyl, arylthioalkyl, heterocyclylthioalkyl, arylalkylsulfonylalkyl, heterocyclylalkylsulfonylalkyl, arylalkylthioalkyl, heterocyclylalkylthioalkyl, cycloalkyl, cycloalkenyl, heterocyclyl, heterocyclenyl, amidino, $R_k^a R_{k+1}^a N$—, $R_k^a N$=, $R_k^a R_{k+1}^a N$-alkyl, $R_k^a R_{k+1}^a NC(=O)$— or $R_k^a R_{k+1}^a NSO_2$—, where $R_k^a$ and $R_{k+1}^a$ independently of each other represent "amino group substituent", the meanings of which are defined in this section, for example, hydrogen, optionally substituted alkyl, optionally substituted aryl, optionally substituted aralkyl, optionally substituted heteroaralkyl or $R_k^a R_{k+1}^a$N-substituent in which $R_k^a$ could be acyl or aroyl, the meaning of $R_{k+1}^a$ is defined above, or "cyclic system substituents" are $R_k^a R_{k+1}^a$NC(=O)— or $R_k^a R_{k+1}^a$NSO$_2$—, where $R_k^a$ and $R_{k+1}^a$ together with the N-atom they are attached to, via $R_k^a$ and $R_{k+1}^a$ give rise to 4-7-membered heterocyclyl or hetrocyclenyl.

"Electrophilic substituent" means a chemical radical attached to the scaffold as a result of a reaction with an electrophilic reagent, for example, one selected from a group of organic acids or their derivatives (anhydrides, imidazolides, acid chlorides), organic sulfonic acid esters or chlorides, organic haloformates, organic isocyanates and organic isothiocyanates.

"Substituted amino group" means $R_k^a R_{k+1}^a$N-group where $R_k^a$ and $R_{k+1}^a$ are the substituents of amino group, the meanings of which are defined in this section.

"Substituted carboxy group" means C(O)OR-group. Substituted carboxyl has substituent R selected from alkenyl, alkyl, aryl, heteroaryl, heterocyclyl, the meanings of which are defined in this section.

"Substituted mercapto group" means SR, S(O)R or S(O$_2$)R group where substituent R represents alkenyl, alkyl, aryl, heteroaryl, heterocyclyl, the meanings of which are defined in this section.

"Protective group" (PG) means a chemical radical attached to a scaffold or synthetic intermediate for temporary protection of amino group in multifunctional compounds, including, but not limited to: amide substituent, such as formyl, optionally substituted acetyl (for example, trichloroacetyl, trifluoroacetyl, 3-phenylpropionyl and others), optionally substituted benzoyl and others; carbamate substituent, such as: optionally substituted C$_1$-C$_7$-alkoxycarbonyl, for example, methyloxycarbonyl, ethyloxycarbonyl, tert-butyloxycarbonyl, 9-fluorenylmethyloxycarbonyl (Fmoc) and others; optionally substituted C$_1$-C$_7$-alkyl substituent, for example tert-butyl, benzyl, 2,4-dimethoxybenzyl, 9-phenylfluorenyl and others; sulfonyl substituent, for example, benzenesulfonyl, p-toluenesulfonyl and others.

"Protected primary or secondary amine" means a group of the general formula $R_k^a R_{k+1}^a$N—, where $R_k^a$ represents protective group PG, $R_{k+1}^a$ is hydrogen, "amino group substituent", the meaning of which is defined in this section, for example, selected from alkyl, alkenyl, aryl, aralkyl, annelated arylcycloalkenyl, annelated arylcycloalkyl, annelated arylheterocyclenyl, annelated arylheterocyclyl, cycloalkyl, cyckloalkenyl, heteroaralkyl, heteroaryl, annelated heteroarylcycloalkenyl, annelated heteroarylcycloalkyl, annelated heteroarylheterocyclenyl, annelated heteroarylheterocyclyl, heterocyclenyl or heterocyclyl.

"Imino group" means $R_k^a$N= group substituted or not by an "amino group substituent" $R_k^a$, the meaning of which is defined in this section, for example, imino (HN=), methylimino (CH$_3$N=), ethylimino (C$_2$H$_5$N=), benzylimino (PhCH$_2$N=) or phenethylimino (PhCH$_2$CH$_2$N=).

"Inert substituent" ("non-interfering substituent") means a low- or non-reactive radical, including, but not limited to: C$_1$-C$_7$ alkyl, C$_2$-C$_7$ alkenyl, C$_2$-C$_7$ alkynyl, alkoxy, C$_7$-C$_{12}$ aralkyl, substituted by inert substituents aralkyl, C$_7$-C$_{12}$ heterocyclylalkyl, substituted by inert substituents heterocyclylalkyl, C$_7$-C$_{12}$ alkaryl, C$_3$-C$_{10}$ cycloalkyl, C$_3$-C$_{10}$ cycloalkenyl, phenyl, substituted phenyl, toluoyl, xylenyl, biphenyl, C$_2$-C$_{12}$ alkoxyalkyl, C$_2$-C$_{10}$ alkylsulfinyl, C$_2$-C$_{10}$ alkylsulfonyl, (CH$_2$)$_m$—O—(C$_1$-C$_7$ alkyl), —(CH$_2$)$_m$—N(C$_1$-C$_7$ alkyl)$_n$, aryl; aryl substituted by halogen or inert substituent, alkoxy substituted by inert substituent, fluoroalkyl, aryloxyalkyl, heterocyclyl, heterocyclyl substituted by inert substituents and nitroalkyl; where m and n are ranged from 1 to 7. C$_1$-C$_7$ Alkyl, C$_2$-C$_7$ alkenyl, C$_2$-C$_7$ alkynyl, C$_1$-C$_7$ alkoxy, C$_7$-C$_{12}$ aralkyl, C$_7$-C$_{12}$ alkaryl, C$_3$-C$_{10}$ cycloalkyl, C$_3$-C$_{10}$ cycloalkenyl, C$_1$-C$_7$ alkyl substituted by inert substituents, phenyl; phenyl substituted by inert substituents, (CH$_2$)$_m$—O—(C$_1$-C$_7$ alkyl), —(CH$_2$)$_m$—N(C$_1$-C$_7$ alkyl)$_n$, aryl; aryl substituted by inert substituents, heterocyclyl and heterocyclyl substituted by inert substituents are the preferred "non-interfering substituents".

"Carbamoyl" means C(=O)NR$_k^a$R$_{k+1}^a$-group. Carbamoyl may have one or more "carbamoyl substituents" R$_k^a$, and R$_{k+1}^a$, selected from hydrogen alkyl, alkenyl, aryl, heteroaryl, heterocyclyl, the meanings of which are defined in this section.

"Carbamoylazaheterocycle" means azaheterocycle with at least one carbamoyl group as a "cyclic system substituent". The meanings of "azaheterocycle", "cyclic system substituent", and "cabamoyl group" are defined in this section.

"Carboxy" means HOC(=O)— (carboxy) group.

"Carboxyalkyl" means HOC(=O)-alkyl group, in which the meaning of alkyl is defined in this section.

"Carbocycle" means mono- or poly-cyclic system composed of carbon atoms only. Carbocycles could be both aromatic and alicyclic. Alicyclic polycycles may have one or more common atoms. One common atom leads to spiro-carbocycles (for example, spiro[2,2]pentane); two—various condensed systems (for example, decaline); three common atoms—to bridged systems (for example, bicycle[3,3,1]nonane); the greater number of common atoms leads to various polyhedron systems (for example, adamantane). Alicycles could be "saturated", for instance, as cyclohexane, or "partly saturated" as tetraline.

"Combinatorial library" means a collection of compounds produced by parallel synthesis and intended for searching for a hit or leader compound, and for optimization of physiological activity of the hit or leader as well, each compound of the library corresponds to the common scaffold, in this way the library is a collection of related homologues or analogues.

"Methylene radical" means —CH$_2$-group with one or two "alkyl substituents" of the same or different structure, the meanings of which are defined in this section.

"Nonaromatic cycle" (saturated or partly saturated cycle) means nonaromatic mono- or polycyclic system formally generated as a result of complete or partial hydrogenization of unsaturated —C=C— or —C=N— bonds. Nonaromatic cycle may have one or more "cyclic system substituents" and could be annelated to aromatic, heteroaromatic or heterocyclic systems. Cyclohexane and piperidine are examples of nonaromatic cycles; cyclohexene and piperideine—are partly saturated cycles "Non-natural aminoacid" means an aminoacid of not nucleinic origin. D-isomers of natural α-aminoacids, such as aminobutyric acid, 2-aminobutyric acid, γ-aminobutyric acid, N-α-alkylaminoacids, 2,2-dialkyl-α-aminoacids, 1-aminocycloalkylcarboxylic acids, β-alanine, 2-alkyl-β-alanines, 2-cycloalkyl-β-alanines, 2-aryl-β-alanines, 2-heteryl-β-alanines, 2-heterocyclyl-β-alanines and (1-aminocycloalkyl)-acetic acids are the representatives of not natural aminoacids in which the meanings of alkyl, cycloalkyl, aryl, heteroaryl and heterocyclyl are defined in this section.

"Optionally aromatic cycle" means a cycle which could be both aromatic and nonaromatic, the meanings of which are defined in this section.

"Optionally substituted radical" means a radical without or with one or more substituents.

"Optionally annelated (condensed) cycle" means a condensed or noncondensed cycle, the meanings of which are defined in this section.

"Lower alkyl" means a straight or branched alkyl radical with 1-4 carbon atoms.

"Parallel synthesis" means a method for carrying out a chemical synthesis of combinatorial library of individual compounds.

"1,3-Propylene radical" means —$CH_2$—$CH_2$—$CH_2$-group with one or more "alkyl substituents" of the same or different structure, the meanings of which are defined in this section.

"Leader compound" (leader) means a compound of outstanding (maximum) physiological activity associated with a concrete biotarget related to a definite (or several) pathology or disease.

"Hit compound" (hit) means a compound demonstrated the desired physiological activity during the primary screening process.

"Sulfamoyl group" means $R_k^a R_{k+1}^a NSO_2$-group substituted or not by "amino group substituents" $R_k^a$ and $R_{k+1}^a$, the meanings of which are defined in this section.

"Sulfonyl" means R—$SO_2$-group in which R could be selected from alkyl, cycloalkyl, aryl, heteroaryl, heterocyclyl, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, the meanings of which are defined in this section.

"Template" means the common structural fragment of the group of the compounds or compounds forming the combinatorial library.

"Therapeutic cocktail" is a simultaneously administered combination of two or more drug substances with different mechanism of pharmacological action and directed to different biotargets taking part in pathogenesis of the disease.

"Thiocarbamoyl" means $R_k^a R_{k+1}^a NC(=S)$-group. Thiocarbamoyl may have one or more "amino group substituents" $R_k^a$ and $R_{k+1}^a$, the meanings of which are defined in this section, for example, alkyl, alkenyl, aryl, heteroaryl and heterocyclyl the meanings of which are defined in this section.

"Cycloalkyl" means nonaromatic mono- or polycyclic system with 3-10 C— atoms. Cycloalkyl may have one or more "cyclic system substituents" of the same or different structure. Cyclopropyl, cyclobutyl, cyclopentyl, cyclohexyl, decalinyl, norbornyl, adamant-1-yl and others are the representatives of cycloalkyl groups. Cycloalkyl could be annelated to aromatic cycle or heterocycle. Alkyl, aralkoxy, hydroxy or $R_k^a R_{k+1}^a N$— are preferred "cyclic system substituents", the meanings of which are defined in this section.

"Cycloalkylcarbonyl" means cycloalkyl-C(=O)-group, in which the meaning of cycloalkyl is defined in this section. Cyclopropylcarbonyl and cyclohexylcarbonyl are the representatives of cycloalkylcarbonyl groups.

"Cycloalkoxy" means cycloalkyl-O-group, in which the meaning of cycloalkyl is defined in this section.

"Pharmaceutical composition" means a composition including the compound of formula I and, at least, one of the components selected from pharmaceutically acceptable and pharmacologicaly compatible excipients, solvents, diluents, carriers, auxiliary distributing and perceiving means, means acting as a vehicle, such as preserving agents, stabilizers, excipients, grinders, wetting agents, emulsifying and suspending agents, thickeners, sweeteners, flavouring agents, antibacterial agents, fungicides, lubricants, regulators of the prolonged delivery, the choice and suitable proportions of which depends on the nature and the way of administration and dosage. Ethoxylated isostearyl alcohol, polyoxyethene, sorbitol and sorbitol ether, microcrystalline cellulose, aluminum metahydroxide, bentonite, agar-agar and tragacant and the mixtures of thereof as well are examples of suitable suspending agents. Protection against action of microorganisms can be provided by means of various antibacterial and antifungal agents, fore example, parabens, chlorobutanole, sorbic acid, and similar compounds. A composition may include also isotonic agents, such as: sugars, sodium chloride and the same. The prolonged action of the composition can be provided by agents slowing down the absorption of the active ingredient, for example, aluminum monostearate and gelatine. Suitable carriers, solvents, diluents and vehicle agents include water, ethanol, polyalcohols and their mixtures, natural oils (such as olive oil) and organic esters for injection (such as ethyl oleate). Suitable fillers include lactose, milk-sugar, sodium citrate, calcium carbonate, calcium phosphate and similar to them. Starch, alginic acid and its salts, silicates are examples of grinders and distributing means. Suitable lubricants include magnesium stearate, sodium lauryl sulfate, talc and polyethylene glycol with high molecular weight. Pharmaceutical composition for oral, sublingval, transdermal, intramuscular, intravenous, subcutaneous, local or rectal introduction of active ingredient alone or in combination with another active compound could be introduced to humans and animals in a standard form of introduction as a mixture with traditional pharmaceutical carriers. Suitable standard forms of administration include oral forms of introduction such as tablets, gelatin capsules, pills, powders, granules, chewing-gums and peroral solutions or suspensions; sublingval and transbuccal forms of introduction; aerosols; implantants; local, transdermal, subcutaneous, intramuscular, intravenous, intranasal or intraocular forms of introduction and rectal forms of introductions.

"Pharmaceutically acceptable salt" means relatively nontoxic both organic and inorganic salts of acids and bases disclosed in this invention. The salts could be prepared in situ in the processes of synthesis, isolation or purification of compounds or they could be prepared purposely. In particular, bases' salts could be prepared starting from purified base of the disclosed compound and suitable organic or mineral acid. Such salts could be obtained with the following acids: hydrochloric acid, hydrobromic acid, sulfuric acid, nitric acid, phosphoric acid, acetic acid, succinic acid, valeric acid, oleic acid, palmitic acid, stearic acid, lauric acid, boric acid, benzoic acid, lactic acid, p-toluenesulfonic acid, citric acid, maleic acid, fumaric acid, succinic acid, tartaric acid, methanesulphonic acid, malonic acid, salicylic acid, propionic acid, ethanesulphonic acid, benzenesulfonic acid, sulfamic acid and the like (Detailed description of the properties of such salts is given in: Berge S. M., et al., "Pharmaceutical Salts" J. Pharm. Sci., 1977, 66: 1-19). Salts of the disclosed acids could be also prepared by the reaction of purified acids with suitable bases; moreover, metal salts and amine salts could be synthesized too. Sodium, potassium, calcium, barium, magnesium, lithium and aluminum salts could be referred to as metal salts; the preferred metal salts are those of sodium and potassium. Inorganic bases suitable for metal salts preparation include sodium hydroxide, carbonate, bicarbonate; potassium hydroxide, carbonate and bicarbonate, lithium hydroxide, calcium hydroxide, magnesium hydroxide, zinc hydroxide. As organic bases suitable for preparation of the disclosed acids salts amines and amino acids with the basicity high enough to make up stable, pharmaceutically acceptable and nontoxic salts could be used. Ammonia, methylamine, dimethylamine, trimethylamine, ethylamine, diethylamine, triethylamine, benzylamine, dibenzylamine, dicyclohexylamine, piperazine, ethylpiperidine, tris(hydroxymethyl) aminomethane and the like could be referred to such amines. Besides that, some tetraalkylammonium hydroxides such as holine, tetramethylammonium, tetraethylammonium and the like could be used for salts preparation. Lysine, ornithine and agrinine are useful as aminoacids with high basicity.

"Fragment" (scaffold) means a molecular frame typical for the group of compounds or compounds belonging to the combinatorial library.

"1,2-Ethylene radical" means —$CH_2$—$CH_2$-group containing one or more "alkyl substituents" of the same or different structure, the meanings of which are defined in this section.

The purpose of the present invention is new substituted indoles and method for their preparation.

The object in view is achieved by substituted indoles of the general formula 1, racemates, optical isomers or pharmaceutically acceptable salts and/or hydrates thereof:

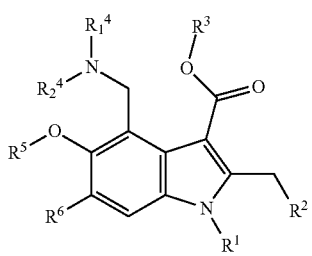

1 wherein:
$R^1$, $R_1^4$ and $R_2^4$ independently of each other represent an amino group substituent selected from hydrogen, optionally substituted alkyl, optionally substituted cycloalkyl, optionally substituted aryl or optionally substituted heterocyclyl, $R_1^4$ and $R_2^4$ together with the N-atom they are attached to, via $R_1^4$ and $R_2^4$ give rise to optionally substituted azaheterocyclyl or guanidyl, $R^2$ is an alkyl substituent selected from the group consisting of hydrogen, optionally substituted mercapto group, optionally substituted amino group, optionally substituted hydroxyl group; $R^3$ is a lower alkyl; $R^5$ represents hydrogen or; $R^5$ together with the O-atom it is attached to, and $R_2^4$ together with the N-atom it is attached to, via $R^5$ and $R_2^4$ give rise to oxazine cycle; $R^6$ is a cyclic system substituent selected from the group consisting of hydrogen, halogen, cyano group, optionally substituted aryl or optionally substituted heterocyclyl with the exception of the compounds of the general formula A.

The preferable substituted indoles are ethyl 5-hydroxy-1H-indole-3-carboxylates of the general formula 1.1 and ethyl 1,2,3,7-tetrahydropyrrolo[3,2-f][1,3]benzoxazine-5-carboxylates of the general formula 1.2, either racemates, optical isomers, or pharmaceutically acceptable salts and/or hydrates thereof.

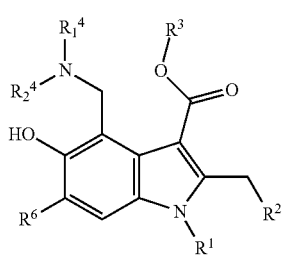

1.1

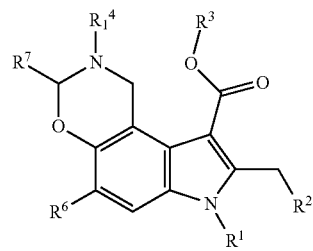

1.2 wherein:
$R^1$, $R^2$, $R^3$, $R_1^4$, $R_2^4$, and $R^6$ are each as defined above; $R^7$ is a cyclic system substituent selected from hydrogen, optionally substituted alkyl, optionally substituted cycloalkyl, optionally substituted aryl or optionally substituted heterocyclyl.

The preferable substituted indoles are ethyl 4-(aminomethyl)-6-aryl(or heterocyclyl)-5-hydroxy-1H-indole-3-carboxylates of the general formula 1.1.1 or ethyl 9-aryl(or heterocyclyl)-1,2,3,7-tetrahydropyrrolo[3,2-f][1,3]benzoxazine-5-carboxylates of the general formula 1.2.1, either racemates, optical isomers or pharmaceutically acceptable salts and/or hydrates thereof.

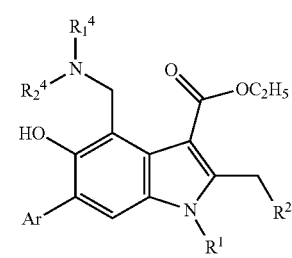

1.1.1

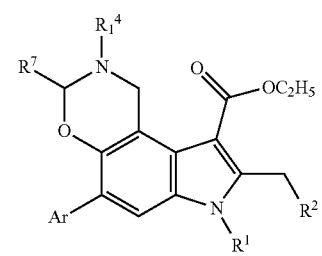

1.2.1 wherein:
$R^1$, $R^2$, $R_1^4$, $R_2^4$ and $R^7$ are each as defined above; Ar represents aryl or 5-6-membered heterocyclyl comprising, at least, one heteroatom selected from the group of N, O or S.

The preferable substituted indoles are ethyl 4-(aminomethyl)-6-aryl(or pyridyl)-5-hydroxy-1-methylindole-3-carboxylates of the general formula 1.1.2 or ethyl 9-aryl(or pyridyl)-7-methyl-1,2,3,7-tetrahydropyrrolo[3,2-f][1,3]benzoxazine-5-carboxylates of the general formula 1.2.2, either racemates, optical isomers or pharmaceutically acceptable salts and/or hydrates thereof.

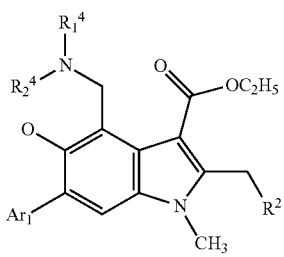

1.1.2

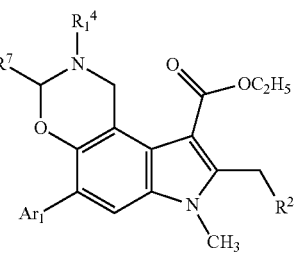

1.2.2 wherein:
$R^2$, $R_1^4$, $R_2^4$ and $R^7$ are each as defined above; $Ar_1$ represents aryl or pyridyl.

The preferable substituted indoles are ethyl 6-aryl(or pyridyl)-2,4-bis(aminomethyl)-5-hydroxy-1-methylindole-3-carboxylates of the general formula 1.1.3 and ethyl 6-(aminomethyl)-9-aryl(or pyridyl)-7-methyl-1,2,3,7-tetrahydropyrrolo[3,2-f][1,3]benzoxazine-5-carboxylates of the general formula 1.2.3 or pharmaceutically acceptable salts and/or hydrates thereof.

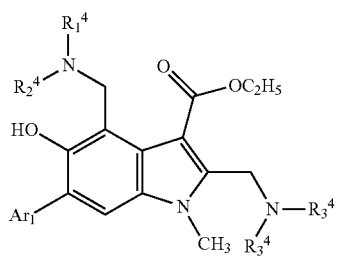

1.1.3

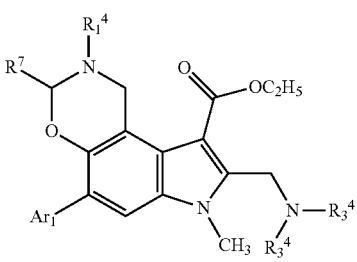

1.2.3 wherein:
$R_1^4$, $R_2^4$, $R^7$ and $Ar_1$ are each as defined above; $R_3^4$ and $R_4^4$ independently of each other represent amino group substituent selected from hydrogen, optionally substituted alkyl, optionally substituted cycloalkyl, optionally substituted aryl or optionally substituted heterocyclyl, or $R_3^4$, $R_4^4$, together with the N-atom they are attached to, via $R_3^4$ and $R_4^4$ give rise to optionally substituted azaheterocyclyl or guanidyl.

The preferable substituted indoles are ethyl 4-(aminomethyl)-6-aryl(or pyridyl)-2-((dimethylamino)methyl)-5-hydroxy-1-methylindole-3-carboxylates of the general formula 1.1.4 ethyl 9-aryl(or pyridyl)- and 6-((dimethylamino)methyl)-7-methyl-1,2,3,7-tetrahydropyrrolo[3,2-f][1,3]benzoxazine-5-carboxylates of the general formula 1.2.4, either racemates, or optical isomers, or pharmaceutically acceptable salts and/or hydrates thereof.

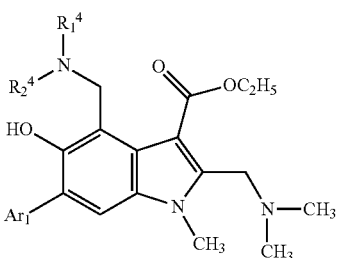

1.1.4

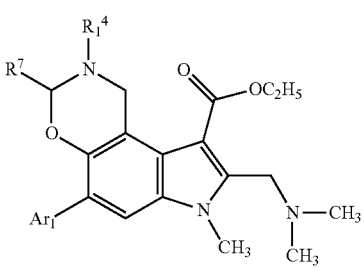

1.2.4 wherein:
$R_1^4$, $R_2^4$, $R^7$ and $Ar_1$ are all as defined above.

The preferable substituted indoles are ethyl 6-aryl(or pyridyl)-2,4-bis((dimethylamino)methyl)-5-hydroxy-1-methylindole-3-carboxylates of the general formula 1.1.5 and ethyl 9-aryl(or pyridyl)-3,7-dimethyl-6-((dimethylamino)methyl)-1,2,3,7-tetrahydropyrrolo[3,2-f][1,3]benzoxazine-5-carboxylates of the general formula 1.2.5 or pharmaceutically acceptable salts and/or hydrates thereof.

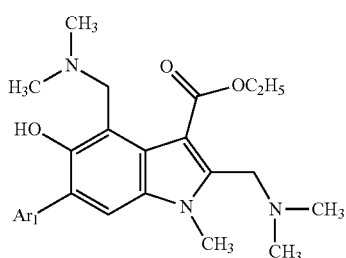

1.1.5

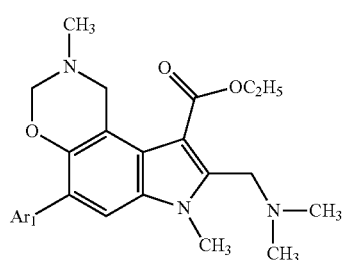

1.2.5 wherein:
$R_1^4$, $R_2^4$, and $Ar_1$ are all as defined above.

The preferable substituted indoles are ethyl 2,4-bis((dimethylamino)methyl)-5-hydroxy-1-methyl-6-(pyridin-3-yl)-indole-3-carboxylate of the formula 1.1.5(1) and ethyl 3,7-dimethyl-6-((dimethylamino)methyl)-9-(pyridin-3-yl)-1,2, 3,7-tetrahydropyrrolo[3,2-f][1,3]benzoxazine-5-carboxylate of the formula 1.2.5(1) or pharmaceutically acceptable salts and/or hydrates thereof.

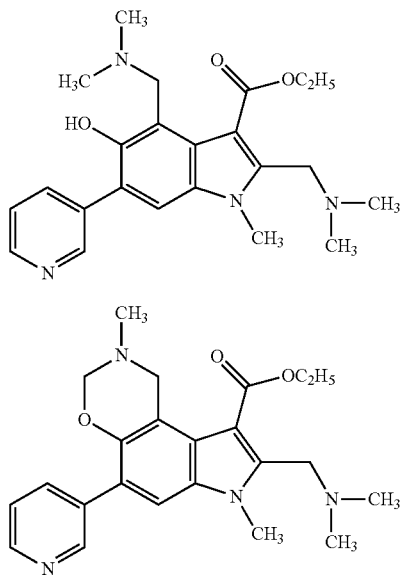

The preferable substituted indoles are ethyl 2-((dimethylamino)methyl)-5-hydroxy-1-methyl-6-(pyridin-3-yl)-4-(pyrrolidin-1-ylmethyl)-indole-3-carboxylate of the formula 1.1.5(2), ethyl 2-((dimethylamino)methyl)-5-hydroxy-4-(1-imidazolylmethyl)-1-methyl-6-(pyridin-3-yl)-indole-3-carboxylate of the formula 1.1.5(3), ethyl 2-((dimethylamino) methyl)-5-hydroxy-4-(guanidylmethyl)-1-methyl-6-(pyridin-3-yl)-indole-3-carboxylate of the formula 1.1.5(4), ethyl 4-((dimethylamino)methyl)-5-hydroxy-1-methyl-6-(pyridin-3-yl)-2-(pyrrolidin-1-ylmethyl)-indole-3-carboxylate of the formula 1.1.5(5) or pharmaceutically acceptable salts and/or hydrates thereof.

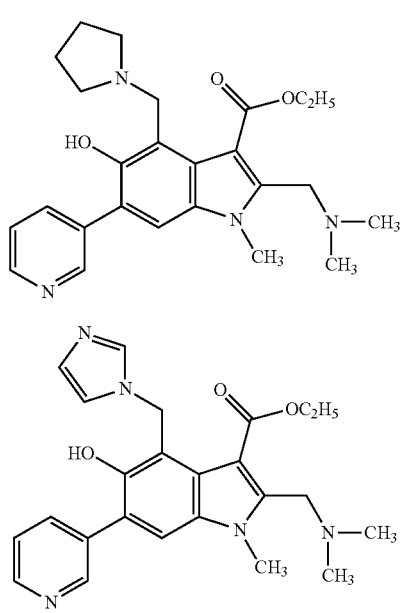

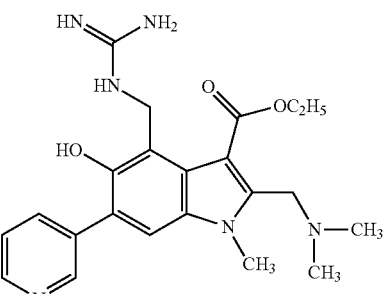

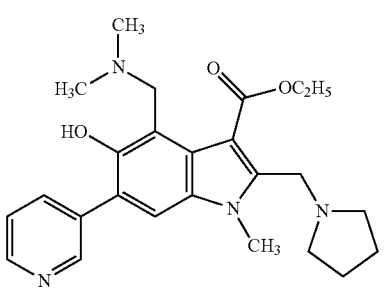

According to the invention the method for preparation of substituted ethyl 4-(aminomethyl)-5-hydroxy-1H-indole-3-carboxylates of the general formula 1.1 consists in interaction of substituted 5-hydroxy-1H-indole-3-carboxylates of the general formula 2 with formaldehyde or paraformaldehyde and amines of the general formula 3 according to the following scheme 1.

Scheme 1

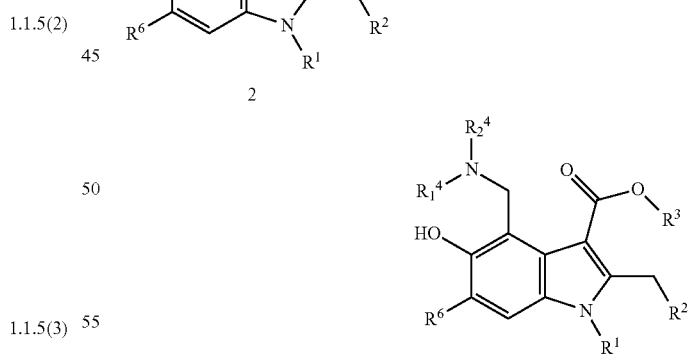

wherein:
$R^1$, $R^2$, $R^3$, $R_1^4$, $R_2^4$ and $R^6$ are all as defined above.

The subject of the invention is also the method for preparation of the general formula 1.2 by interaction of 5-hydroxy-1H-indole-3-carboxylates of the general formula 2 with aldehydes of the general formula 4 and primary amines of the general formula 5 according to the following scheme 2.

Scheme 2

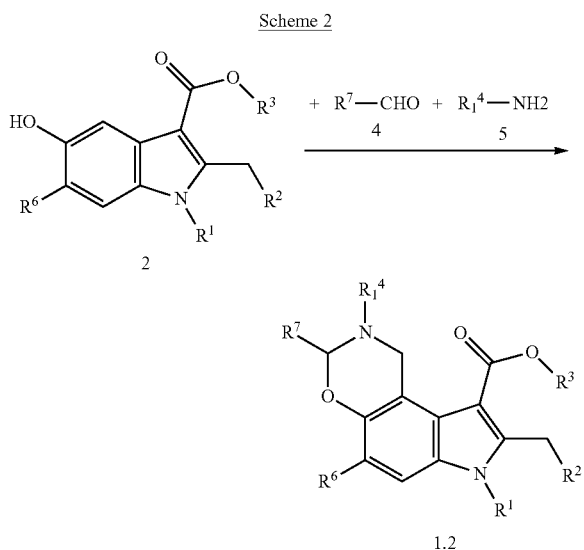

wherein: $R^1$, $R^2$, $R^3$, $R_1^4$, $R^6$ and $R^7$ are all as defined above.

The subject of the invention is also the method for preparation of 1,2,3,7-tetrahydropyrrolo[3,2-f][1,3]benzoxazine-5-carboxylates of the general formula 1.2 by interaction of 4-(aminomethyl)-5-hydroxy-1H-indole-3-carboxylates of the general formula 1.1, where $R_2^4$=H, with aldehydes of the general formula 4 according to the following scheme 3.

Scheme 3

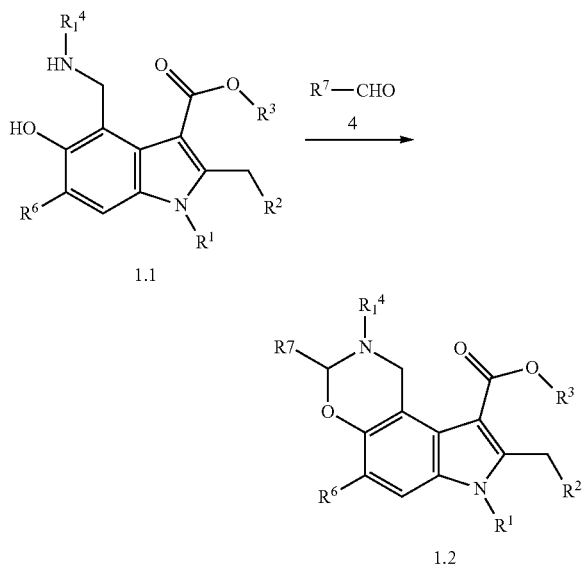

wherein: $R^1$, $R^2$, $R^3$, $R_1^4$, $R^6$ and $R^7$ are all as defined above.

Substituted indole esters of the general formula 1 may give hydrates or pharmaceutically acceptable salts. Both organic and mineral acids could be used for salts preparation, for example, hydrochloric acid, hydrobromic acid, hydriodic acid, sulfuric acid, phosphoric acid, formic acid, acetic acid, propionic acid, trifluoroacetic acid, maleic acid, tartaric acid, methanesulphonic acid, benzenesulfonic acid, p-toluenesulfonic acid. Hydrates are usually formed during recrystallization of compounds of the general formula 1 or their salts from water or water containing solvents.

According to the invention substituted indoles of the general formula 1 could be used as active ingredients of pharmaceutical compositions with antiviral activity including activity in relation to viruses of infectious hepatitises (HCV, HBV), atypical pneumonia (SARS), avian influenza and human immunodeficiency virus (HIV).

The subject of the invention is also pharmaceutical compositions with antiviral activity including activity in relation to viruses of infectious hepatitises (HCV, HBV), atypical pneumonia (SARS), avian influenza, and human immunodeficiency virus (HIV), comprising as an active ingredient, at least, one of azaheterocyclic compounds of the general formula 1 either racemate, or optical isomer, or pharmaceutically acceptable salt and/or hydrate thereof.

The preferable pharmaceutical compositions are the compositions comprising as an active ingredient, at least, one of 5-hydroxy-1H-indole-3-carboxylates of the general formula 1.1 or 1,2,3,7-tetrahydropyrrolo[3,2-f][1,3]benzoxazine-5-carboxylates of the general formula 1.2, either racemates, or optical isomers, or pharmaceutically acceptable salts and/or hydrates thereof.

The preferable pharmaceutical compositions are the compositions comprising as an active ingredient, at least, one of ethyl 4-(aminomethyl)-6-aryl(or heterocyclyl)-5-hydroxy-1H-indole-3-carboxylates of the general formula 1.1.1 or ethyl 9-aryl(or heterocyclyl)-1,2,3,7-tetrahydropyrrolo[3,2-f][1,3]benzoxazine-5-carboxylates of the general formula 1.2.1 either racemates, or optical isomers, or pharmaceutically acceptable salts and/or hydrates thereof.

The preferable pharmaceutical compositions are the compositions comprising as an active ingredient, at least, one of ethyl 4-(aminomethyl)-6-aryl(or pyridyl)-5-hydroxy-1-methylindole-3-carboxylates of the general formula 1.1.2 or ethyl 9-aryl(or pyridyl)-7-methyl-1,2,3,7-tetrahydropyrrolo [3,2-f][1,3]benzoxazine-5-carboxylates of the general formula 1.2.2 or either racemates, or optical isomers, or pharmaceutically acceptable salts and/or hydrates thereof.

The preferable pharmaceutical compositions are the compositions comprising as an active ingredient, at least, one of ethyl 6-aryl(or pyridyl)-2,4-bis(aminomethyl)-5-hydroxy-1-methylindole-3-carboxylates of the general formula 1.1.3 and ethyl 6-(aminomethyl)-9-aryl(or pyridyl)-7-methyl-1,2,3,7-tetrahydropyrrolo[3,2-f][1,3]benzoxazine-5-carboxylates of the general formula 1.2.3, either racemates, or optical isomers, or pharmaceutically acceptable salts and/or hydrates thereof.

The preferable pharmaceutical compositions are the compositions comprising as an active ingredient, at least, one of ethyl 4-(aminomethyl)-6-aryl(or pyridyl)-5-hydroxy-2-((dimethylamino)methyl)-1-methylindole-3-carboxylates of the general formula 1.1.4 and ethyl 9-aryl(or pyridyl)-6-((dimethylamino)methyl)-7-methyl-1,2,3,7-tetrahydropyrrolo[3,2-f][1,3]benzoxazine-5-carboxylates of the general formula 1.2.4, either racemates, or optical isomers, or pharmaceutically acceptable salts and/or hydrates thereof.

The preferable pharmaceutical compositions are the compositions comprising as an active ingredient, at least, one of ethyl 6-aryl(or pyridyl)-2,4-bis((dimethylamino)methyl)-5-hydroxy-1-methylindole-3-carboxylates of the general formula 1.1.5 and ethyl 9-aryl(or pyridyl)-3,7-dimethyl-6-((dimethylamino)methyl)-1,2,3,7-tetrahydropyrrolo[3,2-f][1,3]benzoxazine-5-carboxylates of the general formula 1.2.5 or pharmaceutically acceptable salts and/or hydrates thereof.

The preferable pharmaceutical compositions are the compositions comprising as an active ingredient, at least, one of ethyl 2,4-bis((dimethylamino)methyl)-5-hydroxy-1-methyl- 6-(pyridin-3-yl)-indole-3-carboxylate of the formula 1.1.5(1), ethyl 3,7-dimethyl-6-((dimethylamino)methyl)-9-(pyridin-3-yl)-1,2,3,7-tetrahydropyrrolo[3,2-f][1,3]benzoxazine-5-carboxylate of the formula 1.2.5(1), ethyl 2-((dimethylamino)methyl)-5-hydroxy-1-methyl-6-(pyridin-3-yl)-4-(pyrrolidin-1-ylmethyl)-indole-3-carboxylate of the formula 1.1.5(2), ethyl 2-((dimethylamino)methyl)-5-hydroxy-4-(1-imidazolylmethyl)-1-methyl-6-(pyridin-3-yl)-indole-3-carboxylate of the formula 1.1.5(3), ethyl 2-((dimethylamino)methyl)-5-hydroxy-4-(guanidylmethyl)-1-methyl-6-(pyridin-3-yl)-indole-3-carboxylate of the formula 1.1.5(4) or ethyl 4-((dimethylamino)methyl)-5-hydroxy-1-methyl-6-(pyridin-3-yl)-2-(pyrrolidin-1-ylmethyl)-indole-3-carboxylate of the formula 1.1.5(5) or pharmaceutically acceptable salts and/or hydrates thereof.

Pharmaceutical compositions may include pharmaceutically acceptable excipients. Pharmaceutically acceptable excipients mean diluents, auxiliary agents and/or carriers applied in the sphere of pharmaceutics. According to the invention the pharmaceutical composition together with azaheterocyclic compounds of the general formula 1 may include other active ingredients provided that they do not cause the undesirable effects, such as, allergic reactions.

If required, according to the present invention pharmaceutical compositions can be used in clinical practice in various forms prepared by mixing the compositions with traditional pharmaceutical carries, for example, peroral forms (such as, tablets, gelatinous capsules, pills, solutions or suspensions); forms for injections (such as, solutions or suspensions for injections, or a dry powder for injections which requires only addition of water for injections before utilization); local forms (such as, ointments or solutions).

The carriers used in pharmaceutical compositions, according to the present invention, represent carriers which are applied in the sphere of pharmaceutics for preparation of the commonly used forms including: binding agents, greasing agents, disintegrators, solvents, diluents, stabilizers, suspending agents, colorless agents, taste flavors are used for peroral forms; antiseptic agents, solubilizers, stabilizers are used in forms for injections, base materials, diluents, greasing agents, antiseptic agents are used in local forms.

The purpose of the present invention is also the method for preparation of pharmaceutical compositions.

The object in view is achieved by mixing an active ingredient with an excipient and/or solvent, the distinctive feature of which consists in utilization as an active ingredient, at least, one of azaheterocyclic compounds of the general formula 1, either racemate, or optical isomer, or pharmaceutically acceptable salt and/or hydrate thereof.

According to the invention the pharmaceutical compositions comprising as an active ingredient, at least, one azaheterocyclic compound of the general formula 1 either racemate, or optical isomer, or pharmaceutically acceptable salt and/or hydrate thereof is used for preparation of drug substances in the form of tablets, sheaths or injections placed in pharmaceutically acceptable packing, for prophylaxis and treatment of various virus diseases, including the diseases induced by viruses of infectious hepatitises (HCV, HBV), atypical pneumonia (SARS), avian influenza and human immunodeficiency virus (HIV).

The subject of the invention is also therapeutic cocktails for prophylaxis and treatment of virus diseases, including the diseases induced by viruses of infectious hepatitises (HCV, HBV), atypical pneumonia (SARS), avian influenza and a human immunodeficiency virus (HIV), comprising as one of the components a drug substance, prepared on the basis of a pharmaceutical composition, an active ingredient of which is, at least, one of the azaheterocyclic compounds of the general formula 1, either racemate, or optical isomer, or pharmaceutically acceptable salt and/or hydrate thereof.

Therapeutic cocktails for prophylaxis and treatment of hepatitis C(HCV), along with drug substances disclosed in the invention, may include: inosine-5-monophosphate dehydrogenase inhibitors, for example, Ribavirin (is permitted) and Ribamidine; inhibitors of NS3 protease of hepatitis C, for example, Telaprevir, Siluprevir and SCH-503034; inhibitors of RNK-polimerazy NS5B, for example, XTL-2125; alpha-glucosidase inhibitors, for example, aminocarbohydrate Selgozivir; and also TLR-receptor agonists, hepatoprotectors, cyclosporines, various proteins (for example, interferons), antibodies, vaccines etc.

Therapeutic cocktails for prophylaxis and treatment of hepatitis B (HBV), along with drug substance, disclosed in the invention, may include: reversal-transcriptase inhibitors, for example, Lamivudine and Tenofovir; DNA polymerase inhibitors, for example, Telbivudine, Entecavir and Adefovir dipivoxil; immunostimulative drugs, for example, Serocion; and also angiogenesis inhibitors, hepatoprotectors, various proteins (for example, interferons), antibodies, vaccines etc.

According to the invention the method for prophylaxis and treatment of virus diseases of humans and animals, induced by viruses of infectious hepatitises (HCV, HBV), human immunodeficiency virus (HIV), avian influenza and atypical pneumonia (SARS), consists in introduction to humans or warm-blooded animal of drug substances in the form of tablets, sheaths or injections comprising as an active ingredient, at least, one azaheterocyclic compound of the general formula 1, either racemate, or optical isomer, or pharmaceutically acceptable salt and/or hydrate thereof, or therapeutic cocktails including these drug substances.

The drug substances could be administered perorally or parenterally (for example, intravenously, subcutaneously, intraperitoneally or locally). The clinical dosage of the active ingredient of azaheterocyclic compounds of the general formula 1 could be corrected depending on therapeutic efficiency and bioavailability of the active ingredients in an organism, rate of their exchange and deducing from organism, and depending on the age, sex and the severity of the patient's symptoms; the daily dosage for adults falls within the range of about 10 to about 500 mg of the active ingredient, preferably of about 50 to about 300 mg. Therefore, according to the present invention during the preparation of pharmaceutical compositions as units of dosage it is necessary to keep in mind the above effective dosage, so that each unit of dosage should contain of about 10 to about 500 mg of azaheterocyclic compound of the general formula 1, preferably 50~300 mg. In accordance with the recommendation of a physician or pharmacist the above dosage can be taken several times during the definite time intervals (preferably—from one to six times).

BEST EMBODIMENT OF THE INVENTION

Below the invention is described by means of specific examples, which illustrate but not limit the scope of the invention.

Figure 2:
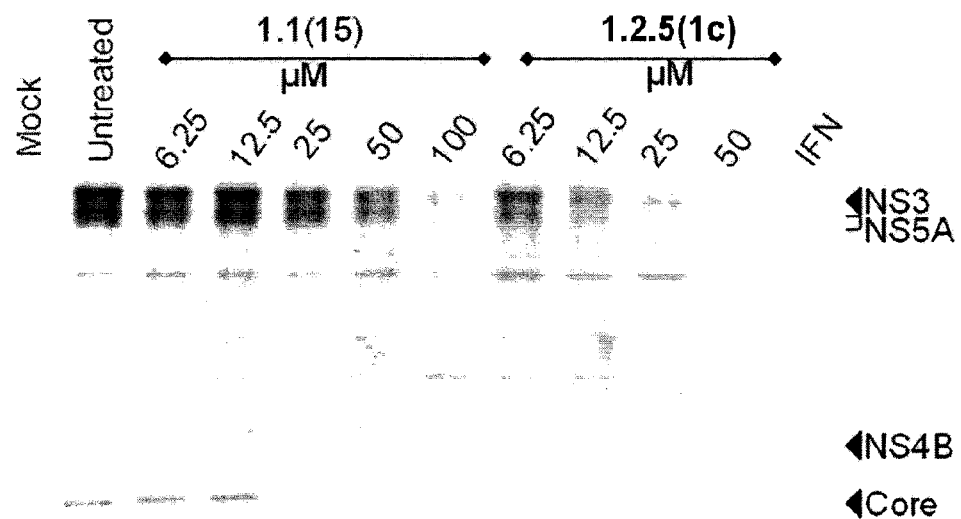
Figure 3:
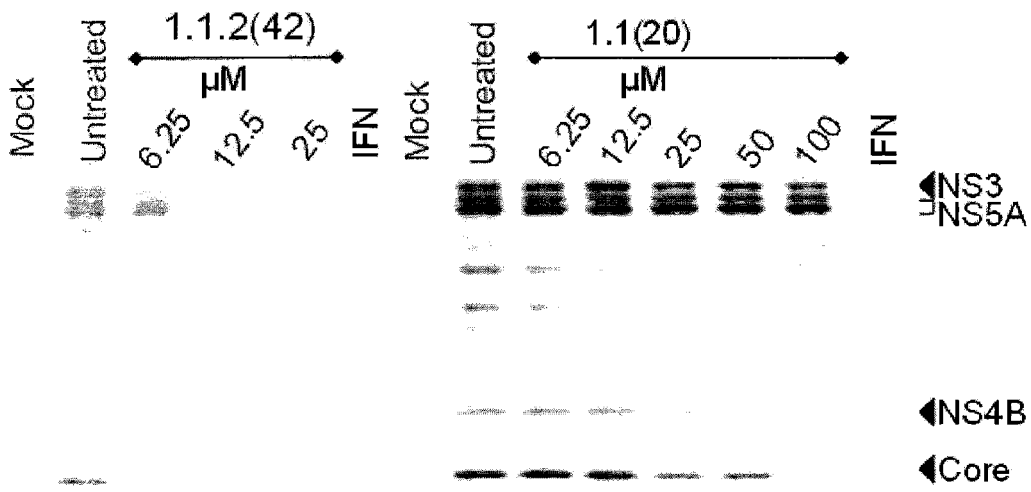
Figure 4:
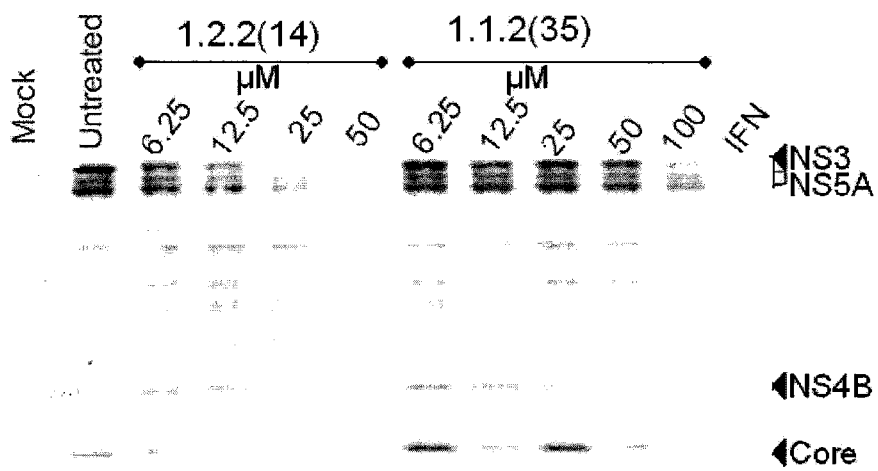
Figure 5:
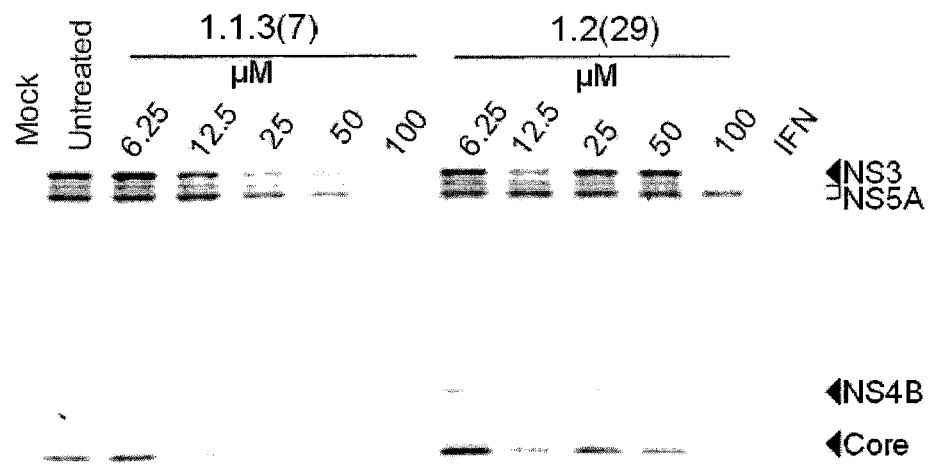
Figure 6:
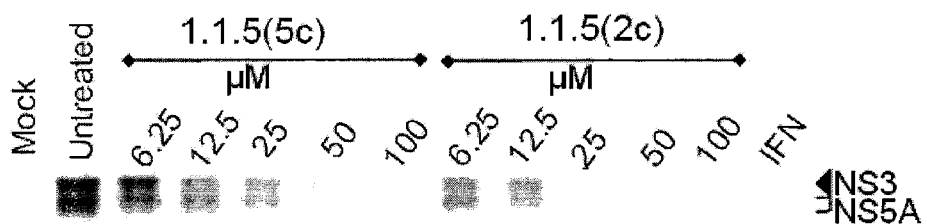
Figure 7:
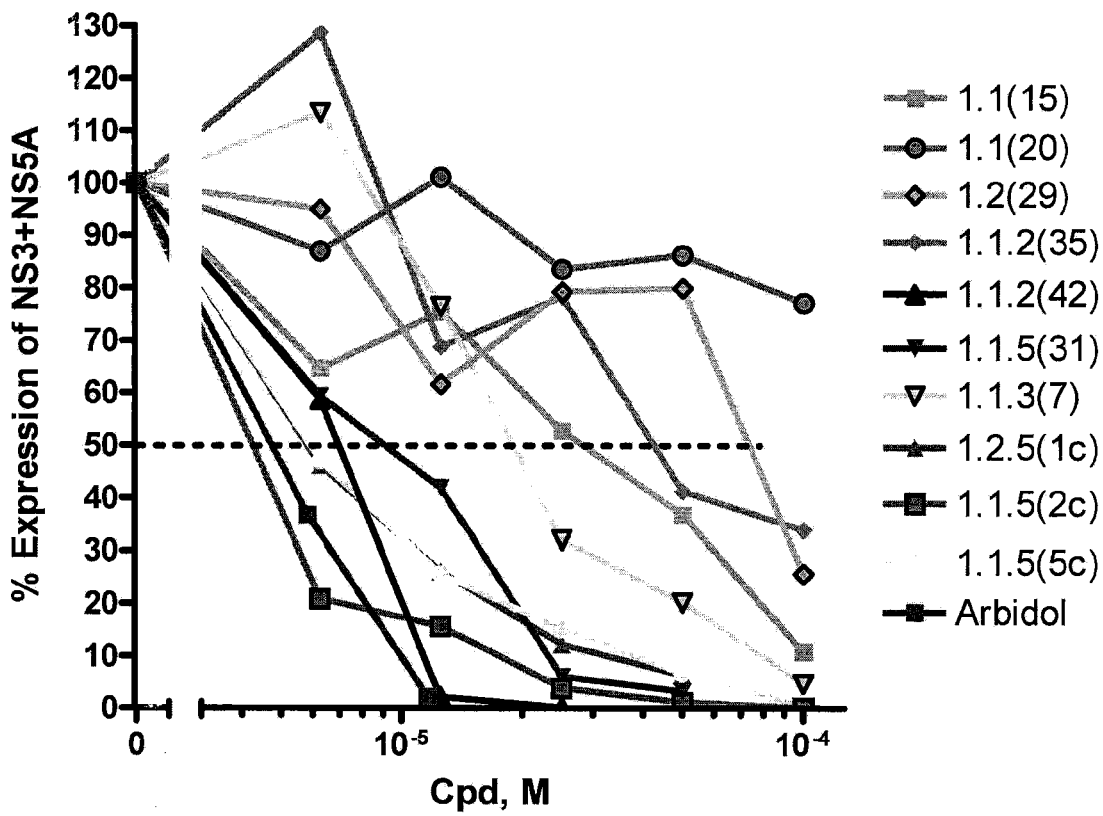
Figure 8:
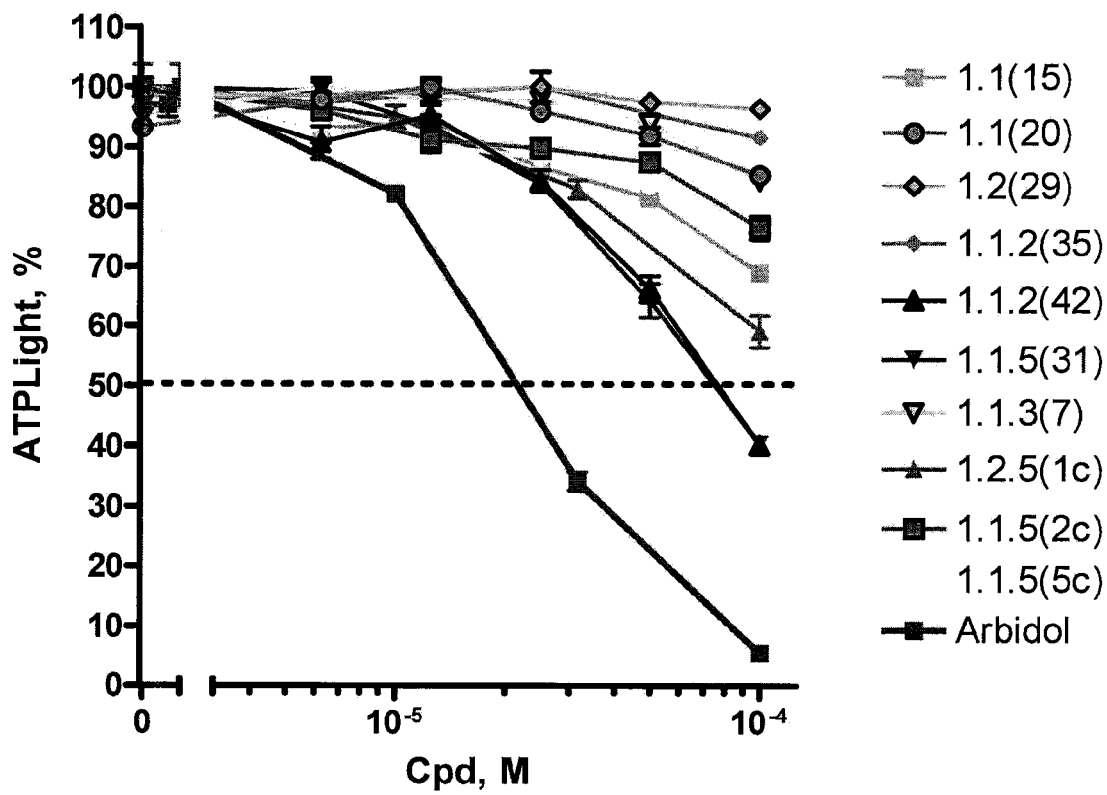

The invention is illustrated by the following figures:

FIG. 1. Western-analysis of Arbidol effectiveness (analogue) 1;

FIG. 2. Western-analysis of compounds 1.1(15) and 1.2.5 (1c) effectiveness;

FIG. 3. Western-analysis of compounds 1.1.2(42) and 1.1 (20) effectiveness;

FIG. 4. Western-analysis of compounds 1.2.2(14) and 1.1.2 (35) effectiveness;

FIG. 5. Western-analysis of compounds 1.1.3(7) and 1.2 (29) effectiveness;

FIG. 6. Western-analysis of compounds 1.1.5(5c) and 1.1.5 (2c) effectiveness;

FIG. 7. Concentration dependence of viral protein (NS3+ NS5a) inhibition by some compounds of the general formula 1;

FIG. 8. Concentration dependence of cytotoxicity of some compounds of the general formula 1.

EXAMPLE 1

Preparation of combinatorial library of substituted 2-(aminomethyl)-5-hydroxy-1H-indole-3-carboxylates of the general formula 1.1. 0.357 Mmol of ester 2, 0.43 mmol of secondary amine 3 and 0.43 mmol of formaldehyde in the form of formalin dissolved in 3 ml of dioxane were stirred and warmed at 70-80° C. for 12-48 h. Monitoring of the reaction was carried out by means of LCMS. After the process was completed the reaction mixture was diluted with water, the separated precipitate was filtered off and recrystallized from the proper solvent or purified by chromatography. As a result of parallel synthesis a combinatorial library of substituted 1H-indole-3-carboxylates of the general formula 1.1 was prepared, including: ethyl 6-bromo-4-((dimethylamino)methyl)-5-hydroxy-2-(hydroxymethyl)-1-methyl-1H-indole-3-carboxylate hydrochloride 1.1(1), LC-MS, m/z 386 (M+H), $^1$H NMR (DMSO-D$_6$, 300 MHz): 9.37 (br, 1H), 9.10 (br, 1H), 8.03 (s, 1H), 8.66 (s, 1H), 5.48 (s, 1H), 4.94 (s, 2H), 4.90 (s, 2H), 4.33 (q, J=5.3 Hz, 2H), 3.83 (s, 3H), 2.75 (s, 6H), 1.36 (t, J=5.3 Hz, 3H); ethyl 4-((dimethylamino)methyl)-5-hydroxy-1-methyl-2-(phenylthiomethyl)-6-(pyrimidin-5-yl)-1H-indole-3-carboxylate 1.1.1(7), LCMS, m/z 477 (M+H); ethyl 4-((dimethylamino)methyl)-5-hydroxy-1-methyl-2-(phenylthiomethyl)-6-(pyridin-3-yl)-1H-indole-3-carboxylate 1.1.2(5), LCMS, m/z 476 (M+H); ethyl 4-((dimethylamino)methyl)-5-hydroxy-1-methyl-2-(phenylthiomethyl)-6-(pyridin-4-yl)-1H-indole-3-carboxylate hydrochloride 1.1.2(6), LCMS, m/476 (M+H); ethyl 5-hydroxy-4-((3-(hydroxymethyl)piperidin-1-yl)methyl)-1-methyl-2-(phenylthiomethyl)-6-(pyridin-3-yl)-1H-indole-3-carboxylate 1.1.2(23), LC-MS, m/z 546 (M+H); ethyl 5-hydroxy-4-((methylamino)methyl)-1-methyl-2-(phenylsulfonylmethyl)-6-(pyridin-3-yl)-1H-indole-3-carboxylate hydrochloride 1.1.2(29), LC-MS, m/z 494 (M+H), NMR-$^1$H (DMSO): 9.53 (br.s, 1H), 9.11 (s, 1H); 8.88 (br.m, 2H); 8.85 (d, J=5.9 Hz, 1H), 8.77 (d, J=8.1 Hz, 1H), 8.09 (m, 1H), 7.95 (s, 1H), 7.72-7.79 (m, 3H), 7.611-7.65 (m, 2H), 5.41 (s, 2H), 4.61 (t, J=5.9 Hz, 2H), 4.11 (q, J=7.0 Hz, 2H), 3.73 (s, 3H); 2.59 (t, J=5.1 Hz, 3H), 1.28 (t, J=7.0 Hz, 3H); ethyl 5-hydroxy-4-((dimethylamino)methyl)-1-methyl-2-(phenylsulfonylmethyl)-6-(pyridin-3-yl)-1H-indole-3-carboxylate hydrochloride 1.1.2(31), LC-MS, m/z 508 (M+H), $^1$H NMR (DMSO-D$_6$): 9.57 (br, 1H), 9.30 (br, 1H), 9.17 (s, 1H), 8.88 (d, J=3.9 Hz, 1H), 8.76 (d, J=5.7 Hz, 1H), 8.10 (m, 1H), 7.96 (s, 1H), 7.75-7.82 (m, 3H), 7.64-7.67 (m, 2H), 5.45 (s, 2H), 4.96 (s, 2H), 4.16 (q, J=5.1 Hz, 2H), 3.78 (s, 3H), 2.79 (s, 6H), 1.32 (t, J=5.1 Hz, 3H); ethyl 5-hydroxy-2-(hydroxymethyl)-1-methyl-4-((dimethylamino)methyl)-6-(pyridin-3-yl)-1H-indole-3-carboxylate hydrochloride 1.1.2(37), LCMS, m/z 370 (M+H), NMR-$^1$H (DMSO): 9.35 (br.s, 1H), 9.10 (s, 1H); 8.84 (d, J=5.1 Hz, 1H), 8.78 (br.m, 2H); 8.73 (d, J=8.4 Hz, 1H), 8.08 (m, 1H), 7.90 (s, 1H), 4.97 (s, 2H), 4.63 (br.t, 2H), 4.33 (q, J=7.0 Hz, 2H), 3.88 (s, 3H); 2.61 (br.t, 1H), 1.36 (t, J=7.0 Hz, 3H); ethyl 5-hydroxy-1-methyl-4-((methylamino)methyl)-6-(pyridin-3-yl)-2-(pyrrolidin-1-ylmethyl)-1H-indole-3-carboxylate hydrochloride 1.1.3(16), LCMS, m/z 423 (M+H), NMR-$^1$H (DMSO): 11.24 (br.m, 1H), 9.57 (br.s, 1H), 9.13 (d, J=1.8 Hz, 1H); 8.96 (br.m, 2H); 8.87 (d, J=5.5 Hz, 1H), 8.81 (m, 1H), 8.14 (m, 1H), 8.04 (s, 1H), 4.95 (d, J=4.8 Hz, 2H), 4.71 (t, J=5.1 Hz, 2H), 4.41 (q, J=7.0 Hz, 2H), 4/07 (s, 3H); 3.46 (m, 2H), 3.24 (m, 2H), 2.60 (t, J=5.1 Hz, 3H), 2.02 (m, 2H), 1.96 (m, 2H), 1.39 (t, J=7.0 Hz, 3H); ethyl 5-hydroxy-1-methyl-4-((methylamino)methyl)-2-(morpholin-4-ylmethyl)-6-(pyridin-3-yl)-1H-indole-3-carboxylate hydrochloride 1.1.3(18), LC-MS, m/z 439 (M+H), NMR-$^1$H (DMSO): 11.46 (br.m, 1H); 9.57 (br.s, 1H), 9.12 (d, J=1.5 Hz, 1H); 8.96 (br.m, 2H), 8.87 (d, J=5.5 Hz, 1H), 8.08 (m, 1H), 8.13 (m, 1H), 8.04 (s, 1H), 4.91 (br.s, 2H), 4.71 (t, J=5.5 Hz, 2H), 4.42 (q, J=7.0 Hz, 2H), 4.07 (s, 3H); 3.85-4.05 (m, 4H), 3.27-3.40 (m, 4H); 2.60 (t, J=5.1 Hz, 3H), 1.40 (t, J=7.0 Hz, 3H); ethyl 2-((dimethylamino)methyl)-5-hydroxy-1-methyl-4-((methylamino)methyl)-6-(pyridin-3-yl)-1H-indole-3-carboxylate hydrochloride 1.1.4(2), LC-MS, m/z 397 (M+H), NMR-1H (DMSO): 10.84 (br.s, 1H), 9.57 (br.s, 1H), 9.12 (d, J=1.8 Hz, 1H); 8.96 (br.m, 2H); 8.87 (d, J=5.5 Hz, 1H), 8.78 (m, 1H), 8.13 (m, 1H), 8.04 (s, 1H), 4.89 (br.s, 2H), 4.72 (dr.t, J=5.1 Hz, 2H), 4.41 (q, J=7.0 Hz, 2H), 3.73 (s, 3H); 2.81 (br.s. 2.60 (t, J=5.5 Hz, 3H), 1.41 (t, J=7.0 Hz, 3H); ethyl 2-((dimethylamino)methyl)-5-hydroxy-1-methyl-6-(pyridin-3-yl)-4-(pyrrolidin-1-ylmethyl)-1H-indole-3-carboxylate hydrochloride 1.1.5(2c), LC-MS, m/z 437 (M+H), NMR-$^1$H (DMSO): 10.72 (br.s (m?), 1H), 9.84 (br.m, 1H), 9.67 (br.s (m?), 1H); 9.18 (d, J=1.8 Hz, 1H); 8.88 (d, J=5.5 Hz, 1H), 8.82 (m, 1H), 8.14 (m, 1H), 8.03 (s, 1H), 5.13 (d, J=5.1 Hz, 2H), 4.89 (d, J=4.8 Hz, 2H), 4.41 (q, J=7.0 Hz, 2H), 4.04 (s, 3H); 3.39 (m, 2H), 3.21 (m, 2H), 2.82 (d, J=4.0 Hz, 6H), 2.0 (m, 2H), 1.88 (m, 2H), 1.41 (t, J=7.0 Hz, 3H); ethyl 4-((dimethylamino)methyl)-5-hydroxy-1-methyl-6-(pyridin-3-yl)-2-(pyrrolidin-1-ylmethyl)-1H-indole-3-carboxylate hydrochloride 1.1.5(5c), LC-MS, m/z 437 (M+H), NMR-$^1$H (DMSO): 11.06 (br.m, 1H); 9.63 (br.m, 1H), 9.40 (br.s, 1H), 9.16 (s, 1H); 8.87 (d, J=5.5 Hz, 1H), 8.78 (d, J=8.1 Hz, 1H), 8.12 (m, 1H), 8.03 (s, 4H), 5.04 (d, J=4.0 Hz, 2H), 4.95 (d, J=4.4 Hz, 2H), 4.41 (q, J=7.0 Hz, 2H), 4.05 (s, 3H); 3.47 (m, 2H), 3.25 (m, 2H); 2.76 (d, J=4.0 Hz, 6H), 1.9-2.1 (m, 4H); 1.40 (t, J=7.0 Hz, 3H) and other 1H-indole-3-carboxylates of the general formula 1.1, some of them are presented in Table 1.

EXAMPLE 2

Preparation of combinatorial library of 1,2,3,7-tetrahydropyrrolo[3,2-f][1,3]benzoxazine-5-carboxylates of the general formula 1.2

A. 0.357 Mmol of ester 2, 0.89 mmol of aldehyde 4, 0.43 mmol of primary amine 5 and 3 ml of dioxane were stirred and warmed at 70-80° C. for 12-48 h. Monitoring of the reaction was carried out by means of LCMS. After the process was completed the reaction mixture was diluted with water, the separated precipitate was filtered off and recrystallized from the proper solvent or purified by chromatography. As a result of parallel synthesis a combinatorial library of substituted pyrrolo[3,2-f][1,3]benzoxazines 1.2 was prepared, including: ethyl 3,7-dimethyl-9-(pyridin-3-yl)-6-(phenylsulfonylmethyl)-1,2,3,7-tetrahydropyrrolo[3,2-f][1,3]benzoxazine-5-carboxylate methyl sulfonate 1.2.2(14), LCMS, m/z 506 (M+H), $^1$H NMR (DMSO-D$_6$): 9.16 (s, 1H), 8.89 (d, J=5.7 Hz, 1H), 8.75 (d, J=8.1 Hz, 1H), 8.08 (m, 1H), 7.94 (s, 1H), 7.62-7.83 (m, 5H), 5.45 (s, 2H), 5.26 (s, 2H), 4.83 (s, 2H), 4.10 (q, J=7.1 Hz, 2H), 3.82 (s, 3H), 2.97 (s, 3H), 2.36 (s, 6H), 1.30 (t, J=7.1 Hz, 3H), ethyl 3,7-dimethyl-9-(pyridin-3-yl)-6-(hydroxymethyl)-1,2,3,7-tetrahydropyrrolo[3,2-f][1,3]

benzoxazine-5-carboxylate methyl sulfonate 1.2.2(16), LCMS, m/z 382 (M+H), $^1$H NMR (DMSO-D$_6$): 9.12 (s, 1H), 8.85 (d, J=4.5 Hz, 1H), 8.66 (d, J=7.8 Hz, 1H), 8.03 (dd, J$_1$=7.5 Hz, J$_2$=6.0 Hz, 1H), 7.89 (s, 1H), 5.25 (s, 2H), 4.98 (s, 2H), 4.87 (s, 2H), 4.34 (q, J=7.0 Hz, 2H), 3.91 (s, 3H), 2.97 (s, 3H), 2.55 (t, J=5.4 Hz, 1H), 2.34 (s, 6H), 1.38 (t, J=7.0 Hz, 3H); ethyl 3,7-dimethyl-9-(pyridine-3-yl)-6-(pyrrolidin-1-ylmethyl)-1,2,3,7-tetrahydropyrrolo[3,2-f][1,3]benzoxazine-5-carboxylate hydrochloride 1.2.3(4), LCMS, m/z 435 (M+H), NMR $^1$H (DMSO): 8.72 (s, 1H), 8.46 (d, J=4.8 Hz, 1H), 7.92 (d, J=7.7 Hz, 1H), 7.40 (m, 1H), 7.38 (s, 1H), 4.71 (s, 2H), 4.23 (q, J=7.5 Hz, 2H), 4.14 (s, 2H), 3.97 (s, 2H), 3.76 (s, 3H), 2.44 (m, 4H), 2.42 (s, 3H), 1.62 (m, 4H), 1.29 (t, J=7.5 Hz, 3H); ethyl 3,7-dimethyl-6-((dimethylamino)methyl)-9-(pyridin-3-yl)-1,2,3,7-tetrahydropyrrolo[3,2-f][1,3]benzoxazine-5-carboxylate hydrochloride 1.2.5(1c), LCMS, m/z 409 (M+H), NMR $^1$H (DMSO): 10.41 (br. s, 1H), 9.06 (d, J=1.5 Hz, 1H), 8.80 (d, J=4.4 Hz, 1H), 8.56 (d, J=7.3 Hz, 1H), 7.96 (s, 1H), 7.95 (m, 1H), 5.21 (s, 2H), 4.82 (s, 4H), 4.39 (q, J=7.5 Hz, 2H), 4.02 (s, 3H), 2.88 (s, 3H), 2.82 (s, 6H), 1.41 (t, J=7.5 Hz, 3H); ethyl 7-benzyl-9-bromo-3-methyl-6-((1-methylpiperazin-4-yl)methyl)-1,2,3,7-tetrahydropyrrolo[3,2-f][1,3]benzoxazine-5-carboxylate 1.2(6), LCMS, m/z 542 (M+H); ethyl 9-bromo-6-((dimethylamino)methyl)-3-methyl-7-phenyl-1,2,3,7-tetrahydropyrrolo[3,2-f][1,3]benzoxazine-5-carboxylate 1.2(21), LC-MS, m/z 473 (M+H); ethyl 9-bromo-3,7-dimethyl-6-((pyridin-4-yl)methyl)-1,2,3,7-tetrahydropyrrolo[3,2-f][1,3]benzoxazine-5-carboxylate 1.2(18), LCMS, m/z 460 (M+H); ethyl 3,7-dimethyl-6-(phenylsulfonylmethyl)-9-cyano-1,2,3,7-tetrahydropyrrolo[3,2-f][1,3]benzoxazine-5-carboxylate 1.2(27), LCMS, m/z 422 (M+H); ethyl 9-bromo-3,7-dimethyl-6-((phenylamino)methyl)-1,2,3,7-tetrahydropyrrolo[3,2-f][1,3]benzoxazine-5-carboxylate 1.2(23), LCMS, m/z 459 (M+H); ethyl 3,7-dimethyl-9-(pyridin-4-yl)-6-(phenylsulfonylmethyl)-1,2,3,7-tetrahydropyrrolo[3,2-f][1,3]benzoxazine-5-carboxylate 1.2 (5), LCMS, m/z 513 (M+H) and other pyrrolo[3,2-f][1,3]benzoxazines 1.2, some of them are presented in Table 1.

B. 0.357 Mmol of the corresponding ester 1.1 and 0.43 mmol of aldehyde 4 in 3 ml of dioxane were stirred and warmed at 70-80° C. for 3-48 h. Monitoring of the reaction was carried out by means of LCMS. After the process was completed the reaction mixture was diluted with water, the separated precipitate was filtered off and recrystallized from the proper solvent or purified by chromatography. As a result of parallel synthesis a combinatorial library of substituted pyrrolo[3,2-f][1,3]benzoxazines 1.2 was prepared, among them: ethyl 9-bromo-2-butyl-3,7-dimethyl-6-((phenylamino)methyl)-1,2,3,7-tetrahydropyrrolo[3,2-f][1,3]benzoxazine-5-carboxylate 1.2(24), LCMS, m/z 515 (M+H); ethyl 9-bromo-3,7-dimethyl-2-phenyl-6-((phenylamino)methyl)-1,2,3,7-tetrahydropyrrolo[3,2-f][1,3]benzoxazine-5-carboxylate 1.2(25), LCMS, m/535 (M+H).

TABLE 1

| No | Formula | MW | LCMS (M + 1) |
|---|---|---|---|
| 1.1(1) | | 421.72 | 386 |
| 1.1(2) | | 517.42 | 518 |
| 1.1(3) | | 517.42 | 518 |

Substituted indoles of the general formula 1

TABLE 1-continued

Substituted indoles of the general formula 1

| No | Formula | MW | LCMS (M + 1) |
|---|---|---|---|
| 1.1(4) | (structure) | 517.42 | 518 |
| 1.1(5) | (structure) | 579.50 | 580 |
| 1.1(6) | (structure) | 579.50 | 580 |
| 1.1(7) | (structure) | 549.44 | 550 |
| 1.1(8) | (structure) | 485.25 | 413 |

TABLE 1-continued

Substituted indoles of the general formula 1

| No | Formula | MW | LCMS (M + 1) |
|---|---|---|---|
| 1.1(9) | | 553.37 | 481 |
| 1.1(10) | | 544.49 | 545 |
| 1.1(11) | | 493.63 | 494 |
| 1.1(12) | | 493.63 | 494 |

TABLE 1-continued

Substituted indoles of the general formula 1

| No | Formula | MW | LCMS (M + 1) |
|---|---|---|---|
| 1.1(13) | | 508.64 | 509 |
| 1.1(14) | | 423.54 | 424 |
| 1.1(15) | | 460.00 | 424 |
| 1.1(16) | | 485.61 | 486 |
| 1.1(17) | | 367.84 | 3321 |

TABLE 1-continued

Substituted indoles of the general formula 1

| No | Formula | MW | LCMS (M + 1) |
|---|---|---|---|
| 1.1(18) | | 461.9 | 426 |
| 1.1(19) | | 499.48 | 427 |
| 1.1(20) | | 431.37 | 359 |
| 1.2(1) | | 448.57 | 449 |
| 1.2(2) | | 610.39 | 449 |

TABLE 1-continued

Substituted indoles of the general formula 1

| No | Formula | MW | LCMS (M + 1) |
|---|---|---|---|
| 1.2(3) | | 459.34 | 460 |
| 1.2(4) | | 483.23 | 411 |
| 1.2(5) | | 585.37 | 513 |
| 1.2(6) | | 650.87 | 542 |

TABLE 1-continued

Substituted indoles of the general formula 1

| No | Formula | MW | LCMS (M + 1) |
|---|---|---|---|
| 1.2(7) | | 526.48 | 527 |
| 1.2(8) | | 599.40 | 527 |
| 1.2(9) | | 595.59 | 596 |
| 1.2(10) | | 577.39 | 505 |

TABLE 1-continued

Substituted indoles of the general formula 1

| No | Formula | MW | LCMS (M + 1) |
|---|---|---|---|
| 1.2(11) | | 466.41 | 394 |
| 1.2(12) | | 540.51 | 541 |
| 1.2(13) | | 540.51 | 541 |
| 1.2(14) | | 495.42 | 496 |

TABLE 1-continued

Substituted indoles of the general formula 1

| No | Formula | MW | LCMS (M + 1) |
|---|---|---|---|
| 1.2(15) | | 490.40 | 491 |
| 1.2(16) | | 440.34 | 441 |
| 1.2(17) | | 514.42 | 515 |
| 1.2(18) | | 459.35 | 460 |
| 1.2(19) | | 447.34 | 448 |

TABLE 1-continued

Substituted indoles of the general formula 1

| No | Formula | MW | LCMS (M + 1) |
|---|---|---|---|
| 1.2(20) | | 524.42 | 525 |
| 1.2(21) | | 545.31 | 473 |
| 1.2(22) | | 512.45 | 513 |
| 1.2(23) | | 458.36 | 459 |
| 1.2(24) | | 514.47 | 515 |

TABLE 1-continued

Substituted indoles of the general formula 1

| No | Formula | MW | LCMS (M + 1) |
|---|---|---|---|
| 1.2(25) | | 534.46 | 535 |
| 1.2(26) | | 472.39 | 473 |
| 1.2(27) | | 421.52 | 422 |
| 1.2(28) | | 457.98 | 422 |
| 1.2(29) | | 429.35 | 357 |
| 1.2(30) | | 404.47 | 405 |

TABLE 1-continued
Substituted indoles of the general formula 1
| No | Formula | MW | LCMS (M + 1) |
|---|---|---|---|
| 1.2(31) | 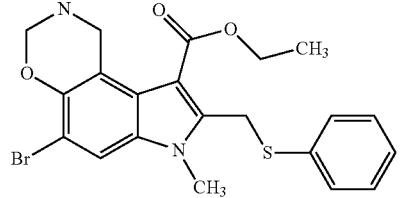 | 489.44 | 490 |
| 1.2(32) | 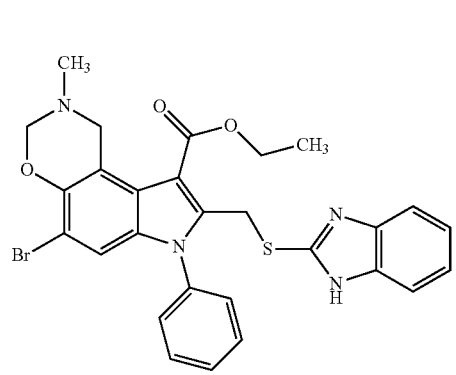 | 577.50 | 578 |
| 1.2(33) | 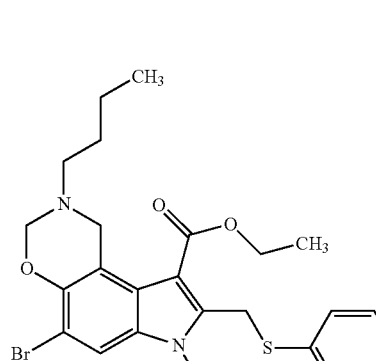 | 517.49 | 518 |
| 1.2(34) | 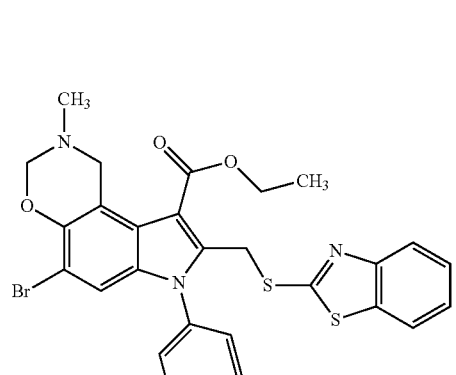 | 594.55 | 595 |

TABLE 1-continued

Substituted indoles of the general formula 1

| No | Formula | MW | LCMS (M + 1) |
|---|---|---|---|
| 1.2(35) | | 551.51 | 552 |
| 1.2(36) | | 514.45 | 515 |
| 1.2(37) | | 531.52 | 532 |
| 1.2(38) | | 475.41 | 476 |
| 1.2(39) | | 551.51 | 552 |

TABLE 1-continued

Substituted indoles of the general formula 1

| No | Formula | MW | LCMS (M + 1) |
|---|---|---|---|
| 1.2(40) | | 491.41 | 492 |
| 1.2(41) | | 543.53 | 544 |
| 1.2(42) | | 507.41 | 508 |
| 1.2(43) | | 541.85 | 542 |
| 1.2(44) | | 458.36 | 459 |

TABLE 1-continued

Substituted indoles of the general formula 1

| No | Formula | MW | LCMS (M + 1) |
|---|---|---|---|
| 1.2(45) | | 492.80 | 493 |
| 1.2(46) | | 461.38 | 462 |
| 1.2(47) | | 481.43 | 482 |
| 1.2(48) | | 512.45 | 513 |
| 1.2(49) | | 509.85 | 510 |

TABLE 1-continued

Substituted indoles of the general formula 1

| No | Formula | MW | LCMS (M + 1) |
|---|---|---|---|
| 1.2(50) | | 546.31 | 510 |
| 1.1.1(1) | | 480.65 | 481 |
| 1.1.1(2) | | 464.59 | 465 |
| 1.1.1(3) | | 514.65 | 515 |
| 1.1.1(4) | | 513.66 | 514 |

TABLE 1-continued

Substituted indoles of the general formula 1

| No | Formula | MW | LCMS (M + 1) |
|---|---|---|---|
| 1.1.1(5) | | 543.69 | 544 |
| 1.1.1(6) | | 514.65 | 515 |
| 1.1.1(7) | | 476.60 | 477 |
| 1.1.1(8) | | 462.57 | 463 |
| 1.1.1(9) | | 525.68 | 526 |

TABLE 1-continued

Substituted indoles of the general formula 1

| No | Formula | MW | LCMS (M + 1) |
|---|---|---|---|
| 1.1.1(10) | | 537.69 | 538 |
| 1.1.1(11) | | 522.61 | 523 |
| 1.1.1(12) | | 631.99 | 523 |
| 1.1.2(1) | | 474.63 | 475 |

TABLE 1-continued

Substituted indoles of the general formula 1

| No | Formula | MW | LCMS (M + 1) |
|---|---|---|---|
| 1.1.2(2) | | 490.63 | 491 |
| 1.1.2(3) | | 517.70 | 518 |
| 1.1.2(4) | | 690.62 | 518 |
| 1.1.2(5) | | 475.61 | 476 |
| 1.1.2(6) | | 512.07 | 476 |

TABLE 1-continued
Substituted indoles of the general formula 1
| No | Formula | MW | LCMS (M + 1) |
|---|---|---|---|
| 1.1.2(7) | 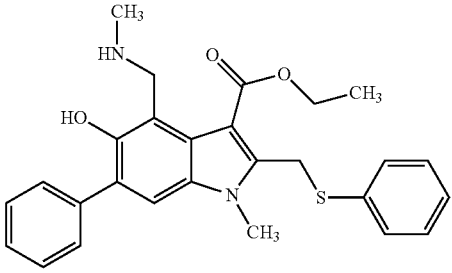 | 460.60 | 461 |
| 1.1.2(8) | 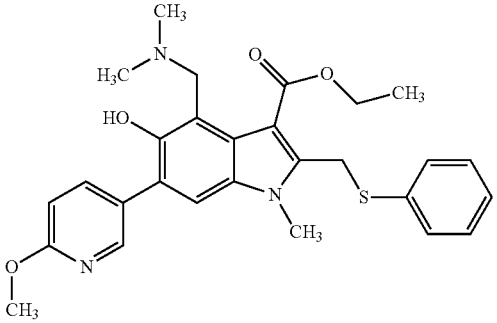 | 505.64 | 506 |
| 1.1.2(9) | 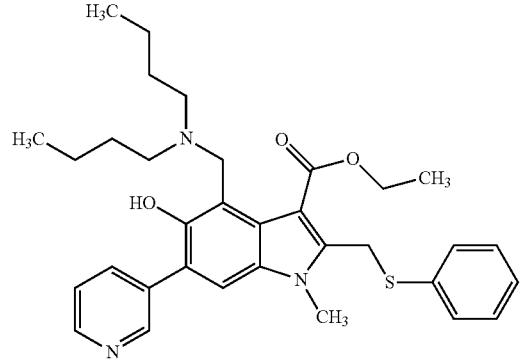 | 559.78 | 560 |
| 1.1.2(10) | 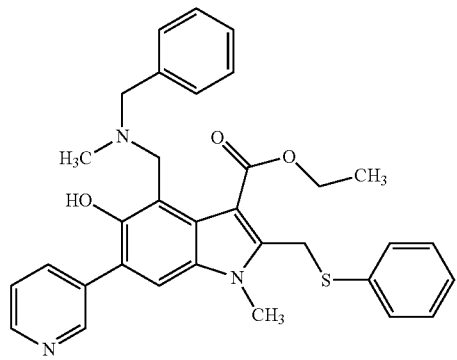 | 551.71 | 552 |

TABLE 1-continued

Substituted indoles of the general formula 1

| No | Formula | MW | LCMS (M + 1) |
|---|---|---|---|
| 1.1.2(11) | | 667.83 | 476 |
| 1.1.2(12) | | 475.61 | 476 |
| 1.1.2(13) | | 489.60 | 490 |
| 1.1.2(14) | | 571.53 | 499 |
| 1.1.2(15) | | 585.56 | 513 |

TABLE 1-continued

Substituted indoles of the general formula 1

| No | Formula | MW | LCMS (M + 1) |
|---|---|---|---|
| 1.1.2(16) | | 571.53 | 499 |
| 1.1.2(17) | | 461.59 | 462 |
| 1.1.2(18) | | 534.51 | 462 |
| 1.1.2(19) | | 461.59 | 462 |
| 1.1.2(20) | | 534.51 | 462 |

TABLE 1-continued

Substituted indoles of the general formula 1

| No | Formula | MW | LCMS (M + 1) |
|---|---|---|---|
| 1.1.2(21) | | 534.51 | 462 |
| 1.1.2(22) | | 559.73 | 560 |
| 1.1.2(23) | | 545.71 | 546 |
| 1.1.2(24) | | 604.77 | 605 |

TABLE 1-continued

Substituted indoles of the general formula 1

| No | Formula | MW | LCMS (M + 1) |
|---|---|---|---|
| 1.1.2(25) | | 462.57 | 463 |
| 1.1.2(26) | | 476.60 | 477 |
| 1.1.2(27) | | 585.98 | 477 |
| 1.1.2(28) | | 571.95 | 464 |
| 1.1.2(29) | | 685.81 | 494 |

TABLE 1-continued

Substituted indoles of the general formula 1

| No | Formula | MW | LCMS (M + 1) |
|---|---|---|---|
| 1.1.2(30) | | 507.61 | 508 |
| 1.1.2(31) | | 699.83 | 508 |
| 1.1.2(32) | | 493.59 | 494 |
| 1.1.2(33) | | 594.52 | 522 |
| 1.1.2(34) | | 603.53 | 531 |

TABLE 1-continued

Substituted indoles of the general formula 1

| No | Formula | MW | LCMS (M + 1) |
|---|---|---|---|
| 1.1.2(35) | | 383.45 | 384 |
| 1.1.2(36) | | 575.67 | 384 |
| 1.1.2(37) | | 369.42 | 370 |
| 1.1.2(38) | | 561.64 | 370 |
| 1.1.2(39) | | 459.55 | 460 |

TABLE 1-continued

Substituted indoles of the general formula 1

| No | Formula | MW | LCMS (M + 1) |
|---|---|---|---|
| 1.1.2(40) | | 543.67 | 544 |
| 1.1.2(41) | | 491.61 | 492 |
| 1.1.2(42) | | 564.53 | 492 |
| 1.2.2(1) | | 472.61 | 473 |
| 1.2.2(2) | | 509.07 | 473 |

TABLE 1-continued
Substituted indoles of the general formula 1
| No | Formula | MW | LCMS (M + 1) |
|---|---|---|---|
| 1.2.2(3) | 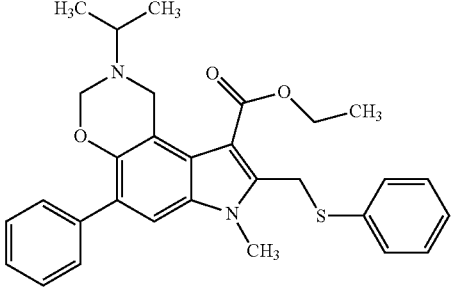 | 500.67 | 501 |
| 1.2.2(4) | 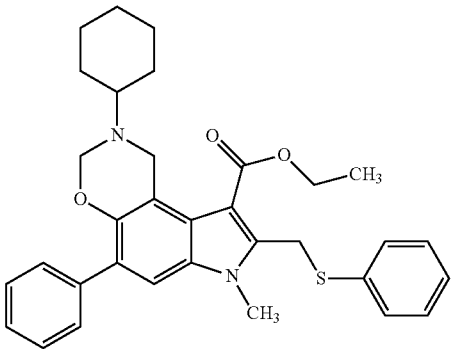 | 540.73 | 541 |
| 1.2.2(5) | 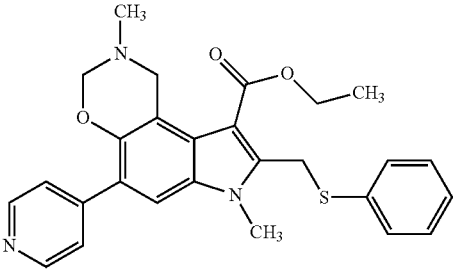 | 473.60 | 474 |
| 1.2.2(6) | 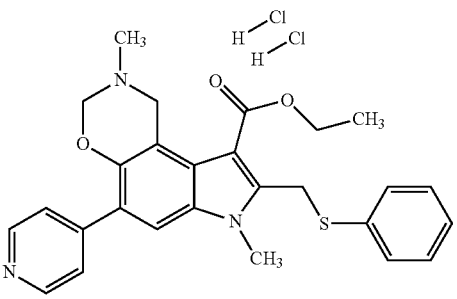 | 546.52 | 474 |
| 1.2.2(7) | 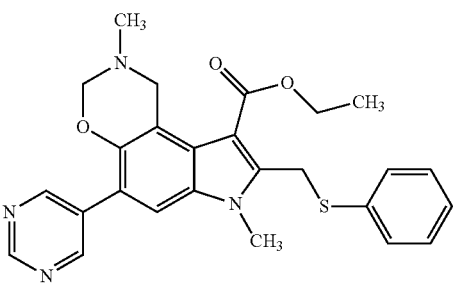 | 474.59 | 475 |

TABLE 1-continued

Substituted indoles of the general formula 1

| No | Formula | MW | LCMS (M + 1) |
|---|---|---|---|
| 1.2.2(8) | | 546.52 | 474 |
| 1.2.2(9) | | 593.97 | 475 |
| 1.2.2(10) | | 474.59 | 475 |
| 1.2.2(11) | | 678.06 | 569 |

TABLE 1-continued

Substituted indoles of the general formula 1

| No | Formula | MW | LCMS (M + 1) |
|---|---|---|---|
| 1.2.2(12) | | 656.81 | 657 |
| 1.2.2(13) | | 505.60 | 506 |
| 1.2.2(14) | | 578.52 | 506 |
| 1.2.2(15) | | 381.44 | 382 |
| 1.2.2(16) | | 573.66 | 382 |

TABLE 1-continued

Substituted indoles of the general formula 1

| No | Formula | MW | LCMS (M + 1) |
|---|---|---|---|
| 1.2.2(17) | | 475.52 | 476 |
| 1.2.2(18) | | 548.44 | 476 |
| 1.1.3(1) | | 382.47 | 383 |
| 1.1.3(2) | | 491.85 | 383 |
| 1.1.3(3) | | 396.49 | 397 |

TABLE 1-continued

Substituted indoles of the general formula 1

| No | Formula | MW | LCMS (M + 1) |
|---|---|---|---|
| 1.1.3(4) | | 505.87 | 397 |
| 1.1.3(5) | | 443.55 | 444 |
| 1.1.3(6) | | 516.47 | 444 |
| 1.1.3(7) | | 505.45 | 433 |
| 1.1.3(8) | | 505.45 | 433 |

TABLE 1-continued

Substituted indoles of the general formula 1

| No | Formula | MW | LCMS (M + 1) |
|---|---|---|---|
| 1.1.3(9) | | 457.58 | 458 |
| 1.1.3(10) | | 458.57 | 459 |
| 1.1.3(11) | | 444.54 | 445 |
| 1.1.3(12) | | 553.92 | 445 |
| 1.1.3(13) | | 458.57 | 459 |

TABLE 1-continued

Substituted indoles of the general formula 1

| No | Formula | MW | LCMS (M + 1) |
|---|---|---|---|
| 1.1.3(14) | | 567.95 | 459 |
| 1.1.3(15) | | 422.53 | 423 |
| 1.1.3(16) | | 531.91 | 423 |
| 1.1.3(17) | | 438.53 | 439 |
| 1.1.3(18) | | 547.91 | 439 |

TABLE 1-continued

Substituted indoles of the general formula 1

| No | Formula | MW | LCMS (M + 1) |
|---|---|---|---|
| 1.1.3(19) | | 452.56 | 453 |
| 1.1.3(20) | | 561.94 | 453 |
| 1.1.3(21) | | 585.93 | 476 |
| 1.1.3(22) | | 598.96 | 490 |
| 1.1.3(23) | | 585.93 | 476 |

TABLE 1-continued

Substituted indoles of the general formula 1

| No | Formula | MW | LCMS (M + 1) |
|---|---|---|---|
| 1.1.3(24) | | 586.92 | 477 |
| 1.2.3(1) | | 394.48 | 395 |
| 1.2.3(2) | | 503.86 | 395 |
| 1.2.3(3) | | 434.54 | 435 |
| 1.2.3(4) | | 543.92 | 435 |

TABLE 1-continued
Substituted indoles of the general formula 1
| No | Formula | MW | LCMS (M + 1) |
|---|---|---|---|
| 1.2.3(5) | 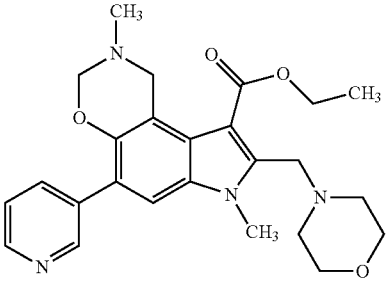 | 450.54 | 451 |
| 1.2.3(6) | 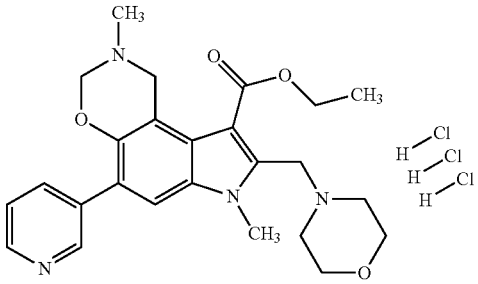 | 559.92 | 451 |
| 1.2.3(7) | 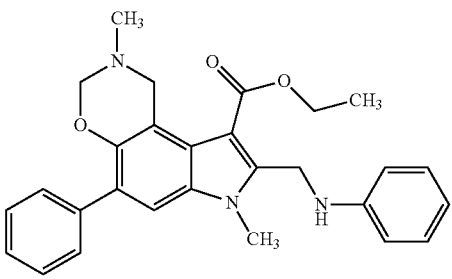 | 455.56 | 456 |
| 1.2.3(8) | 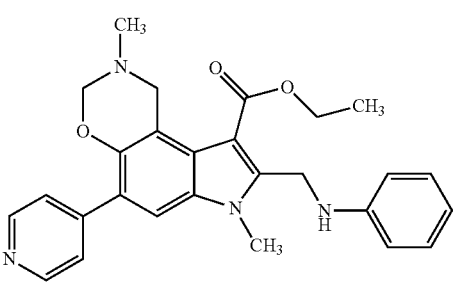 | 456.55 | 456 |
| 1.1.4(1) | 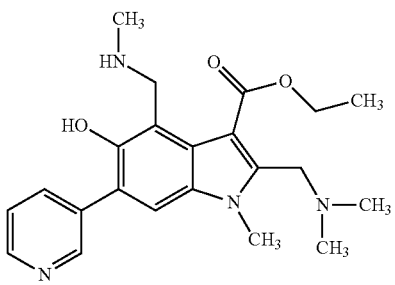 | 396.49 | 397 |

TABLE 1-continued

Substituted indoles of the general formula 1

| No | Formula | MW | LCMS (M + 1) |
|---|---|---|---|
| 1.1.4(2) | (structure) | 505.87 | 397 |
| 1.1.4(3) | (structure) | 542.89 | 434 |
| 1.1.4(4) | (structure) | 542.89 | 434 |
| 1.1.4(5) | (structure) | 543.88 | 435 |
| 1.1.4(6) | (structure) | 533.89 | 425 |

TABLE 1-continued

Substituted indoles of the general formula 1

| No | Formula | MW | LCMS (M + 1) |
|---|---|---|---|
| 1.2.4(1) | | 611.97 | 503 |
| 1.2.4(2) | | 631.43 | 486 |
| 1.2.5(2) | | 408.50 | 409 |
| 1.2.5(2c) | | 517.88 | 409 |
| 1.1.5(1) | | 410.52 | 411 |

TABLE 1-continued

Substituted indoles of the general formula 1

| No | Formula | MW | LCMS (M + 1) |
|---|---|---|---|
| 1.1.5(1c) | | 519.90 | 411 |
| 1.2.5(1) | | 408.50 | 409 |
| 1.2.5(1c) | | 517.88 | 409 |
| 1.1.5(2) | | 436.56 | 437 |
| 1.1.5(2c) | | 545.94 | 437 |

TABLE 1-continued

Substituted indoles of the general formula 1

| No | Formula | MW | LCMS (M + 1) |
|---|---|---|---|
| 1.1.5(3) | | 433.51 | 434 |
| 1.1.5(3c) | | 542.89 | 434 |
| 1.1.5(4) | | 424.51 | 425 |
| 1.1.5(4c) | | 533.89 | 425 |
| 1.1.5(5) | | 436.56 | 437 |

TABLE 1-continued

Substituted indoles of the general formula 1

| No | Formula | MW | LCMS (M + 1) |
|---|---|---|---|
| 1.1.5(5c) | (structure shown) | 545.94 | 437 |

EXAMPLE 3

Examination of antiviral activity of the compounds of the general formula 1. Examination of antiviral activity of the compounds of the general formula 1 was carried out at concentration of 10 mg/ml in relation to virus influenza A in a cell culture MDCK at dilution of virus $10^{-3}$ according to the procedure, described in the following articles [Zotova, S. A; Korneeva, T. M; Shvedov, V. I.; Fadeeva, N. I.; Dineva, I. A.; Fedyakina, I. T.; Kristova, M. L.; Nikolaeva, I. S.; Piters, V. V.; Guskova, T. A. Khim-Farm. Zh. 1995, 29(1), 51-53. PCT WO 2005/087729 A1, 2005.]. Inhibition of viral reproduction by some substituted 1H-indole-3-carboxylic acids of the general formula 1 is shown in Table 2.

TABLE 2

Inhibition of influenza A virus reproduction by substituted 1H-indole-3-carboxylic acids of the general formula 1

| No | Formula | % of inhibition |
|---|---|---|
| 1.1(11) | (structure shown) | <50 |
| 1.1(18) | (structure shown) | <50 |

TABLE 2-continued

Inhibition of influenza A virus reproduction by substituted 1H-indole-3-carboxylic acids of the general formula 1

| No | Formula | % of inhibition |
|---|---|---|
| 1.1.1(2) | | 63 |
| 1.1.1(3) | | 52 |
| 1.1.1(4) | | 66 |
| 1.1.1(5) | | 60 |
| 1.1.1(6) | | 58 |

TABLE 2-continued

Inhibition of influenza A virus reproduction by substituted
1H-indole-3-carboxylic acids of the general formula 1

| No | Formula | % of inhibition |
|---|---|---|
| 1.1.1(7) | | 62 |
| 1.1.1(9) | | 88 |
| 1.1.1(10) | | 100 |
| 1.2(1) | | <50 |
| 1.2(2) | | <50 |

TABLE 2-continued

Inhibition of influenza A virus reproduction by substituted 1H-indole-3-carboxylic acids of the general formula 1

| No | Formula | % of inhibition |
|---|---|---|
| 1.2(5) | | 97 |
| 1.2(6) | | 92 |
| 1.2(7) | | 100 |
| 1.2(8) | | 100 |

TABLE 2-continued
Inhibition of influenza A virus reproduction by substituted
1H-indole-3-carboxylic acids of the general formula 1
| No | Formula | % of inhibition |
|---|---|---|
| 1.2(9) | 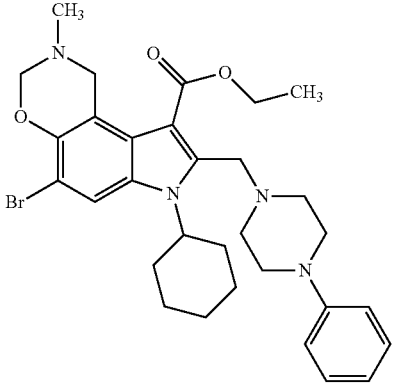 | 62 |
| 1.2(10) | 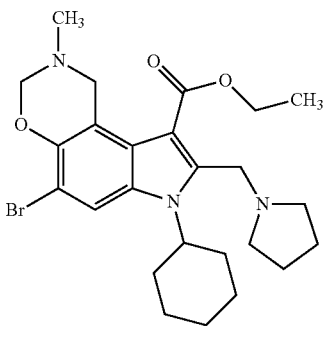 | 81 |
| 1.2(11) | 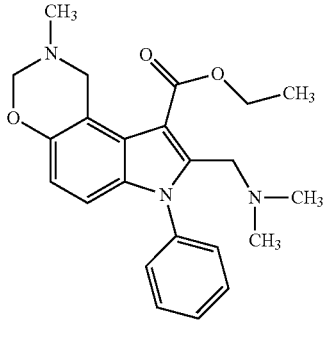 | 77 |
| 1.2(12) | 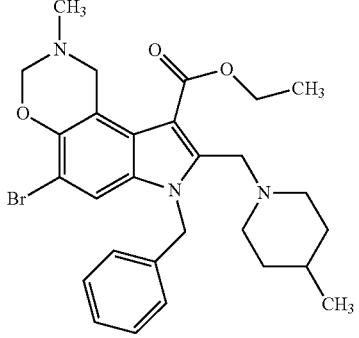 | 85 |

TABLE 2-continued

Inhibition of influenza A virus reproduction by substituted 1H-indole-3-carboxylic acids of the general formula 1

| No | Formula | % of inhibition |
|---|---|---|
| 1.2(13) | | 77 |
| 1.2(14) | | 95 |
| 1.2(16) | | 90 |
| 1.2(17) | | 97 |
| 1.2(18) | | 100 |

TABLE 2-continued
Inhibition of influenza A virus reproduction by substituted
1H-indole-3-carboxylic acids of the general formula 1
| No | Formula | % of inhibition |
|---|---|---|
| 1.2(19) | 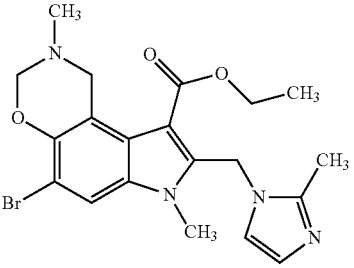 | 88 |
| 1.2(26) | 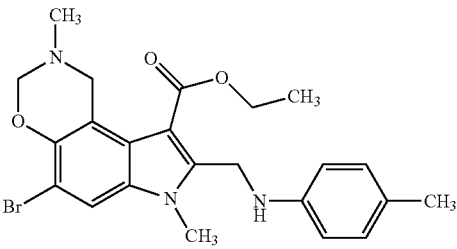 | 100 |
| 1.2(27) | 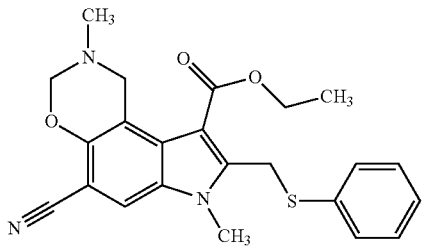 | <50 |
| 1.2(30) | 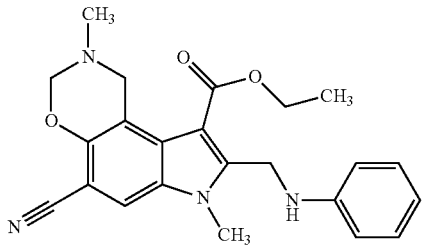 | <50 |
| 1.2(31) | 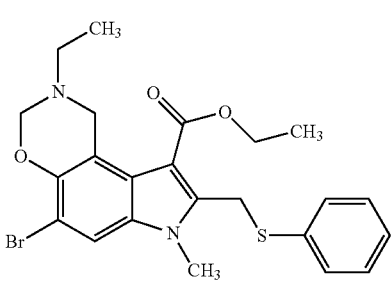 | 100 |

TABLE 2-continued
Inhibition of influenza A virus reproduction by substituted 1H-indole-3-carboxylic acids of the general formula 1
| No | Formula | % of inhibition |
|---|---|---|
| 1.2(32) | 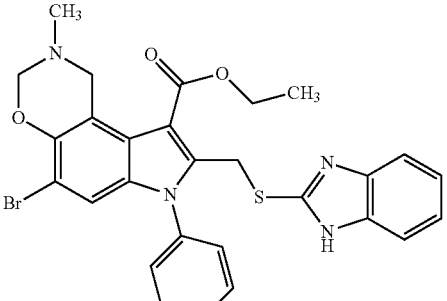 | 65 |
| 1.2(33) | 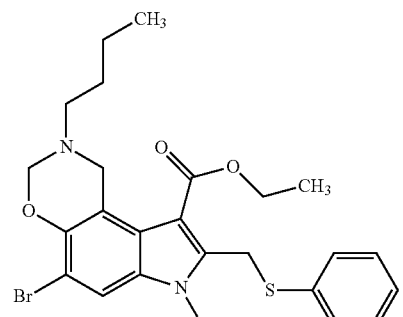 | 95 |
| 1.2(34) | 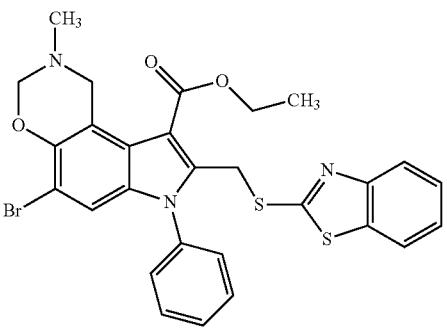 | <50 |
| 1.2(35) | 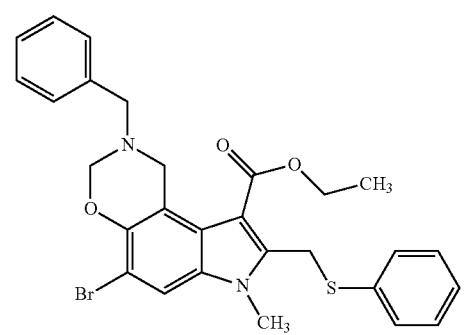 | 98 |

TABLE 2-continued

Inhibition of influenza A virus reproduction by substituted 1H-indole-3-carboxylic acids of the general formula 1

| No | Formula | % of inhibition |
|---|---|---|
| 1.2(36) | | <50 |
| 1.2(37) | | 77 |
| 1.2(38) | | 100 |
| 1.2(39) | | 62 |
| 1.2(41) | | 89 |

TABLE 2-continued

Inhibition of influenza A virus reproduction by substituted 1H-indole-3-carboxylic acids of the general formula 1

| No | Formula | % of inhibition |
|---|---|---|
| 1.2(42) | | 88 |
| 1.2(43) | | 77 |
| 1.2(44) | | 100 |
| 1.2(45) | | 100 |
| 1.2(46) | | 100 |
| 1.2(47) | | 100 |

TABLE 2-continued
Inhibition of influenza A virus reproduction by substituted
1H-indole-3-carboxylic acids of the general formula 1
| No | Formula | % of inhibition |
|---|---|---|
| 1.2(48) | 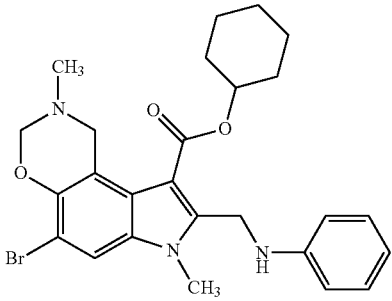 | 76 |
| 1.2(49) | 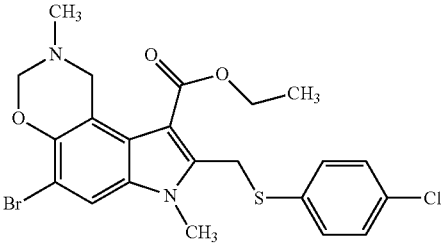 | 90 |
| 1.2.1(1) | 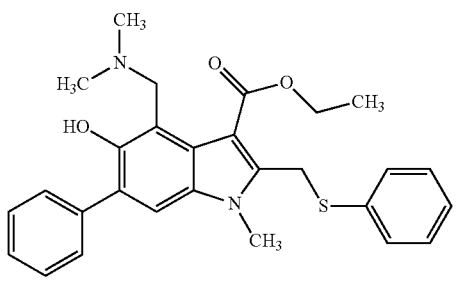 | 96 |
| 1.2.1(2) | 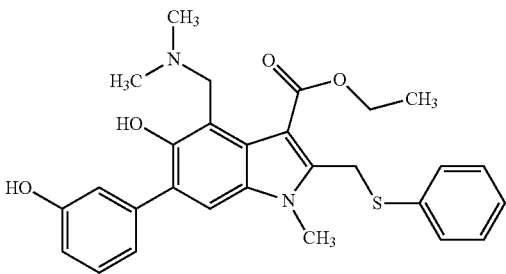 | 51 |
| 1.2.1(3) | 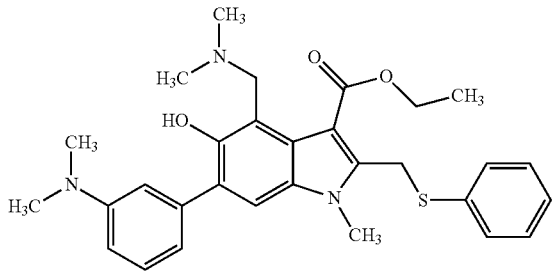 | 77 |

TABLE 2-continued

Inhibition of influenza A virus reproduction by substituted 1H-indole-3-carboxylic acids of the general formula 1

| No | Formula | % of inhibition |
|---|---|---|
| 1.2.1(5) | | 100 |
| 1.2.1(6) | | 100 |
| 1.2.1(8) | | 81 |
| 1.2.1(23) | | 95 |
| 1.2.1(29) | | 88 |

TABLE 2-continued

Inhibition of influenza A virus reproduction by substituted 1H-indole-3-carboxylic acids of the general formula 1

| No | Formula | % of inhibition |
|---|---|---|
| 1.2.2(3) | | 95 |
| 1.2.2(5) | | 100 |
| 1.2.2(7) | | 88 |
| 1.2.2(8) | | 100 |
| 1.2.3(7) | | 90 |

TABLE 2-continued

Inhibition of influenza A virus reproduction by substituted 1H-indole-3-carboxylic acids of the general formula 1

| No | Formula | % of inhibition |
|---|---|---|
| 1.2.3(8) | [structure] | 100 |

4. Determination of antiviral activity of the pharmaceutical composition comprising as an active ingredient one of the compounds of the general formula 1, presented in table 1, was carried out towards viruses of specially cloned human hepatocytes (Huh7.5.1) with an increased sensitivity to infection of virus hepatitis C [Ralf Bartenschlager* and Thomas Pietschmann. Proc Natl Acad Sci USA. 2005 Jul. 12; 102 (28): 9739-9740]. The cells were cultivated in modified Eagle medium Dulbecco (Page 53) (DMEM) containing 9% calf serosity and 1% of nonessential amino acids. The cells were embedded (in amounts of 200,000 cells) in every well of 6-well plate and were left for 24 hours, then the tested compounds in various concentration were added and kept together for 24 hours, after that virus of hepatitis C strain JFH-1 (genotype 2a) was added to the cells, as it was described in [Zhong J, Gastaminza P, Cheng G, Kapadia S, Kato T, Burton D R, Wieland S F, Uprichard S L, Wakita T, Chisari F V: Robust hepatitis C virus infection in vitro. Proc Natl Acad Sci USA 2005, 102:9294-9299], and the cells were incubated for 72 hours at 37° C. After that the cellular medium was removed, the cells were lysed with the buffer, containing 50 mM tris-HCl, pH 7.2; 150 mM NaCl, 0.1% SDS, 0.1% Na deoxycholate, 1% Triton X-100, 17.4 g/ml PMSF and the protein amount was quantitatively determined using BCA Protein Assay (Pierce Biotechnology, USA). Before insertion of the sample on gel, the concentration of every sample was corrected in such a way, that 10 μg of protein was introduced into every well of gel. The samples were agitated with equal volume of the reducing buffer, heated at 95° C. for 7 minutes and subjected to electrophoresis in 4-20% tris-glyceric buffer (Invitrogen, USA). The separated proteins were transferred to 0.45 μM nitrocellulose membrane (Pierce, USA), using the system of semi-dry passage. After that the membranes were blocked with buffer Superblock (Pierce, USA) and incubated with initial mouse antibodies specific to protein virus NS5A (Biodesign International, Saco, Me.; 1:1000 dilution) and Core (Affinity Bioreagents, Golden, Colo.; 1:1000 dilution) and kept additionally at ambient temperature for an hour. Then the membranes were kept with the secondary antimouse immunoglobuline G, conjugated with horse-radish peroxidase (IgG, Pierce, 1:10000 dilution). The developed protein strips were visualizated, using chemiluminescent reagent LumiGlo (Cell Signaling, Danvers, Mass.) and exposition of membranes with x-ray film. Strips were digitized, using software package ImageJ [http://rsb.info.nih.gov/ij/].

The test results are shown in FIGS. 1-8 and in table 3. The values of antiviral activity ($IC_{50}$), toxicity ($TC_{50}$) and therapeutic index ($SI_{50}$=the $HARDWARE_{50}/IC_{50}$) for some of the tested substances are presented in table 3. The data given confirm high efficiency of the new antiviral substances.

TABLE 3

Antiviral activity ($IC_{50}^{HCV}$), toxicity ($TC_{50}$) and therapeutic index ($SI_{50} = TC_{50}/IC_{50}$) for some of the tested compounds.

| No comp. | Formula | $IC_{50}$ uM | $TC_{50}$ | Therapeutic index $SI_{50} = TC_{50}/IC_{50}$ |
|---|---|---|---|---|
| 1.1(15) | [structure] | 28 | >100 | >4 |

TABLE 3-continued
Antiviral activity ($IC_{50}^{HCV}$), toxicity ($TC_{50}$) and therapeutic index
($SI_{50} = TC_{50}/IC_{50}$) for some of the tested compounds.
| No comp. | Formula | $IC_{50}$ uM | $TC_{50}$ | Therapeutic index $SI_{50} = TC_{50}/IC_{50}$ |
|---|---|---|---|---|
| 1.2(29) | 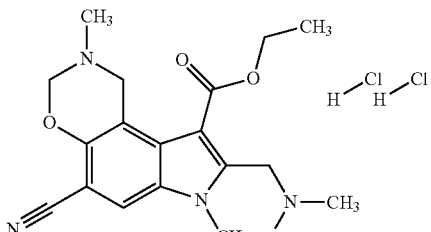 | >100 | >100 | — |
| 1.1.2(35) | 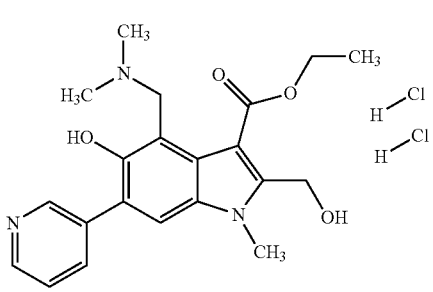 | 6 | >100 | >16 |
| 1.1.2(42) | 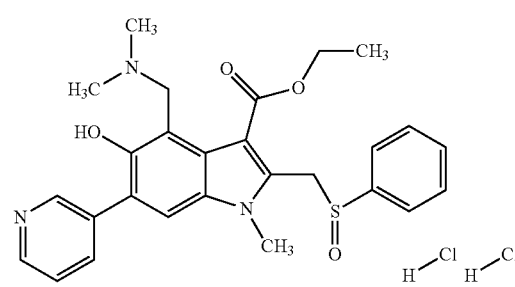 | 18 | >100 | >5 |
| 1.2.2(14) | 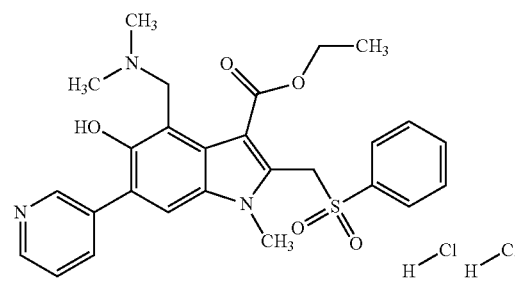 | 43 | >100 | >2 |
| 1.1.3(7) | 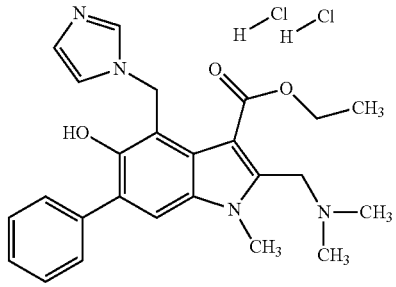 | 72 | >100 | >1.4 |

TABLE 3-continued

Antiviral activity ($IC_{50}^{HCV}$), toxicity ($TC_{50}$) and therapeutic index
($SI_{50} = TC_{50}/IC_{50}$) for some of the tested compounds.

| No comp. | Formula | $IC_{50}$ uM | $TC_{50}$ | Therapeutic index $SI_{50} = TC_{50}/IC_{50}$ |
|---|---|---|---|---|
| 1.2.5(1c) | | 6 | 78 | 13 |
| 1.1.5(2c) | | 7 | 75 | 11 |
| 1.1.5(5c) | | <5 | >100 | >20 |

EXAMPLE 5

Preparation of a drug substance in the form of tablets. Mix together 1600 mg of starch, 1600 mg of the grained lactose, 400 mg of talcum and 1000 mg of ethyl 4-((dimethylamino)methyl)-5-hydroxy-1-methyl-6-(pyridin-3-yl)-2-(pyrrolidin-1-ylmethyl)-1H-indole-3-carboxylate hydrochloride 1.1.5(5c) and press in a brick. The prepared brick was crushed to granules and riddled through sieves, gathering granules of 14-16 mesh size. The obtained granules were pelletised in tablets of suitable form of 560 mg weight each. According to the invention pharmaceutical compositions in the form of tablets comprising as an active ingredient other substituted 1H-indole-3-carboxylic acids of the general formula 1 were prepared in a similar way.

EXAMPLE 6

Preparation of a drug substance in the form of capsules. Carefully mix ethyl 4-((dimethylamino)methyl)-5-hydroxy-1-methyl-6-(pyridin-3-yl)-2-(pyrrolidin-1-ylmethyl)-1H-indole-3-carboxylate hydrochloride 1.1.5(5c) with lactose powder in ratio 2:1 The prepared powdery mixture was packed by 300 mg into gelatinous capsules of suitable size.

EXAMPLE 7

Preparation of a drug substance in the form of compositions for intramuscular, intraperitoneal or hypodermic injections. Mix 500 mg of ethyl 4-((dimethylamino)methyl)-5-hydroxy-1-methyl-6-(pyridin-3-yl)-2-(pyrrolidin-1-ylmethyl)-1H-indole-3-carboxylate hydrochloride 1.1.5(5c) with about 300 mg of chlorobutanole, 2 ml of propylene glycol and 100 ml of water for injections. The prepared solution was filtered and placed in 1 ml ampoules which were sealed up and sterilized in an autoclave.

INDUSTRIAL APPLICABILITY

The invention could be used in medicine, veterinary, biochemistry.

What is claimed is:

1. A substituted indole compound which is an ethyl 4-(aminomethyl)-6-aryl(or heterocyclyl)-5-hydroxy-1H-indole-3-carboxylate of the general formula 1.1.1 or an ethyl 9-aryl(or heterocyclyl)-1,2,3,7-tetrahydropyrrolo[3,2-f][1,3]bezoxazine-5-carboxylate of the general formula 1.2.1, or a racemate, optical isomer, or pharmaceutically acceptable salt thereof:

1.1.1

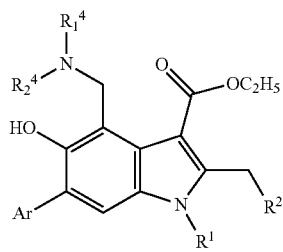

1.2.1

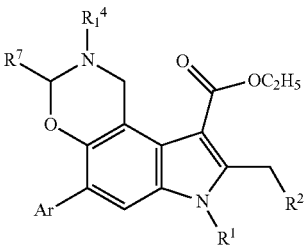

wherein $R^1$, $R_1^4$ and $R_2^4$ are each independently hydrogen, an optionally substituted alkyl, optionally substituted cycloalkyl, optionally substituted aryl or optionally substituted heterocyclyl, or $R_1^4$ and $R_2^4$, together with the N-atom to which they are attached, via $R_1^4$ and $R_2^4$, form optionally substituted azaheterocyclyl or guanidyl;

$R^2$ is hydrogen, an optionally substituted mercapto group, optionally substituted hydroxy group, or optionally substituted amino group, $NR_3^4R_4^4$, wherein $R_3^4$ and $R_4^4$ are each independently hydrogen, an optionally substituted alkyl, optionally substituted cycloalkyl, optionally substituted aryl or optionally substituted heterocyclyl, or $R_3^4$ or $R_4^4$ together with the N-atom to which they are attached, via $R_3^4$ and $R_4^4$, form optionally substituted azaheterocyclyl or guanidyl;

$R^7$ is hydrogen, an optionally substituted alkyl, optionally substituted cycloalkyl, optionally substituted aryl or optionally substituted heterocyclyl; and Ar is an optionally substituted aryl or an optionally substituted 5- or 6-membered heterocyclyl, wherein the heteroatom is N, O or S.

2. The compound of claim 1 which is an ethyl 4-(aminomethyl)-6-aryl(or pyridyl)-5-hydroxy-1-methylindol-3-carboxylate of the general formula 1.1.2 or an ethyl 9-aryl-(or pyridyl)-7-methyl-1,2,3,7-tetrahydropyrrolo[3,2-f][1,3]benzoxazine-5-carboxylate of the general formula 1.2.2, or a racemate, optical isomer, or pharmaceutically acceptable salt thereof:

1.1.2

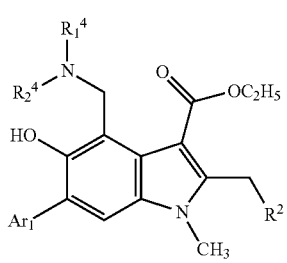

1.2.2

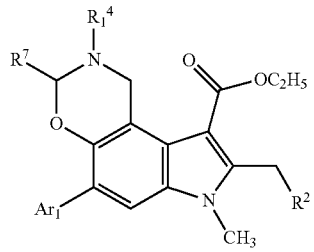

wherein $Ar_1$ is an optionally substituted phenyl or optionally substituted pyridyl.

3. The compound of claim 2 which is an ethyl 6-aryl(or pyridyl)-2,4-bis(aminomethyl)-5-hydroxy-1-methylindole-3-carboxylate of the general formula 1.1.3 or an ethyl 6-(aminomethyl)-9-aryl(or pyridyl)-7-methyl-1,2,3,7-tetrahydropyrrolo[3,2-f][1,3]benzoxazine-5-carboxylate of the general formula 1.2.3, or a racemate, optical isomer, or pharmaceutically acceptable salt thereof:

1.1.3

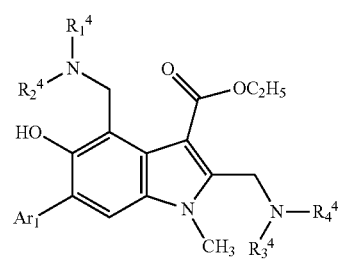

1.2.3

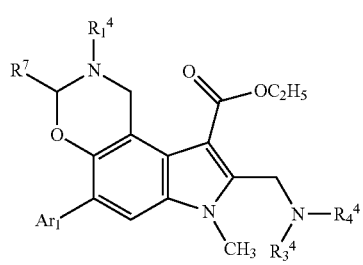

wherein $R_3^4$ and $R_4^4$ are each independently hydrogen, an optionally substituted alkyl, optionally substituted cycloalkyl, optionally substituted aryl or optionally substituted heterocyclyl, or $R_3^4$ or $R_4^4$ together with the N-atom to which they are attached, via $R_3^4$ and $R_4^4$, form optionally substituted azaheterocyclyl or guanidyl.

4. The compound of claim 3 which is an ethyl 4-(aminomethyl)-6-aryl-(or pyridyl)-5-hydroxy-2-((dimethylamino)methyl)-1-methylindole-3-carboxylate of the general formula 1.1.4, or an ethyl 9-aryl-(or pyridyl)-6-((dimethylamino)methyl)-7-methyl-1,2,3,7-tetrahydropyrrolo[3,2-f][1,3]benzoxazine-5-carboxylate of the general formula 1.2.4, or a racemate, optical isomer, or pharmaceutically acceptable salt thereof:

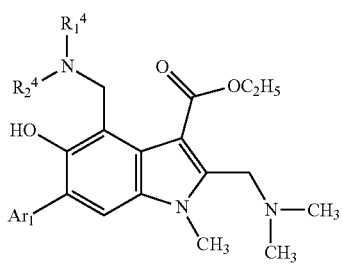
1.1.4

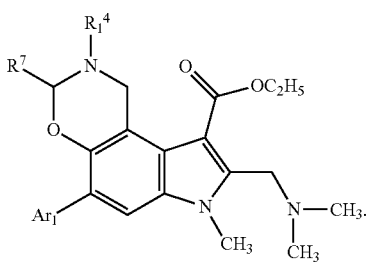
1.2.4

5. The compound of claim 4 which is an ethyl 6-aryl(or pyridyl)-2,4-bis((dimethylamino)methyl)-5-hydroxy-1-methylindole-3-carboxylate of the general formula 1.1.5 or an ethyl 9-aryl(or pyridyl)-3,7-dimethyl-6-((dimethylamino)methyl)-1,2,3,7-tetrahydropyrrolo[3,2-f][1,3]benzoxazine-5-carboxylate of the general formula 1.2.5, or a pharmaceutically acceptable salt thereof:

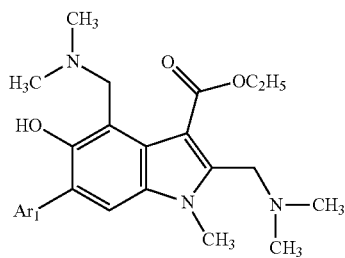
1.1.5

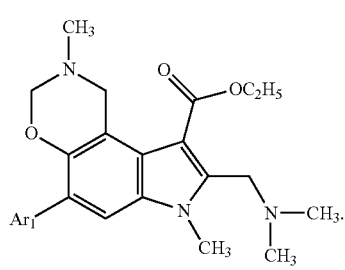
1.2.5

6. The compound of claim 5 which is ethyl 2,4-bis((dimethylamino)methyl)-5-hydroxy-1-methyl-6-(pyridin-3-yl)-1H-indole-3-carboxylate of the formula 1.1.5(1) or ethyl 3,7-dimethyl-6-((dimethylamino)methyl)-9-(pyridin-3-yl)-1,2,3,7-tetrahydropyrrolo[3,2-f][1,3]benzoxazine-5-carboxylate of the formula 1.2.5(1), or a pharmaceutically acceptable salt thereof:

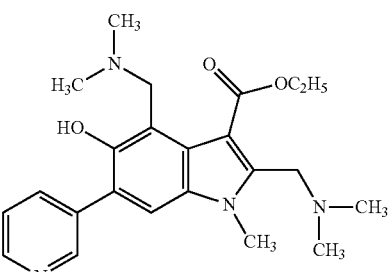
1.1.5(1)

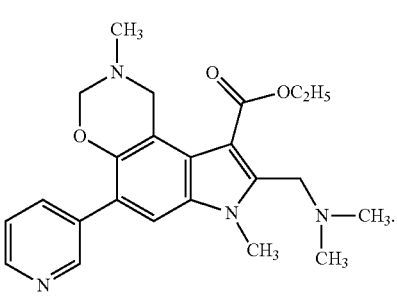
1.2.5(1)

7. The compound of claim 1 which is ethyl 2-((dimethylamino)methyl)-5-hydroxy-1-methyl-6-(pyridin-3-yl)-4-((pyrrolidin-1-yl)methyl)-indole-3-carboxylate of the formula 1.1.5(2), ethyl 2-((dimethylamino)methyl)-5-hydroxy-4-((imidazol-1-yl)methyl)-1-methyl-6-(pyridin-3-yl)-indole-3-carboxylate of the formula 1.1.5(3), ethyl 2-((dimethylamino)methyl)-5-hydroxy-4-(guanidylmethyl)-1-methyl-6-(pyridin-3-yl)-indole-3-carboxylate of the formula 1.1.5(4) or ethyl 4-((dimethylamino)methyl)-5-hydroxy-1-methyl-6-(pyridin-3-yl)-2-((pyrrolidin-1-yl)methyl)-indole-3-carboxylate of the formula 1.1.5(5), or a pharmaceutically acceptable salt thereof:

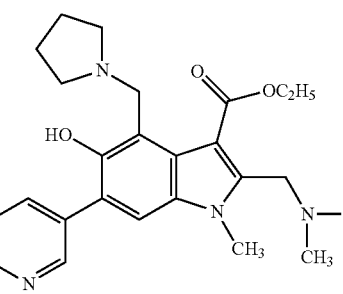
1.1.5(2)

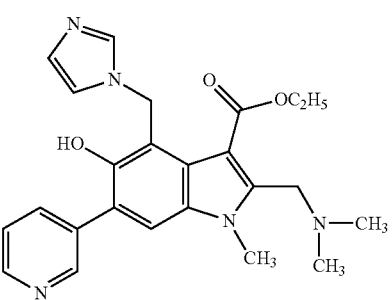
1.1.5(3)

1.1.5(4)
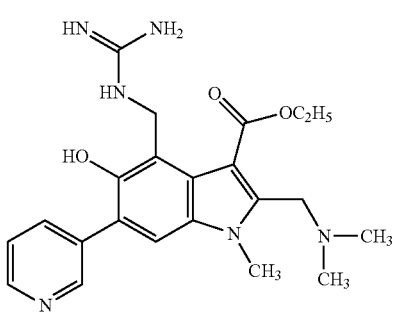

1.1.5(5)
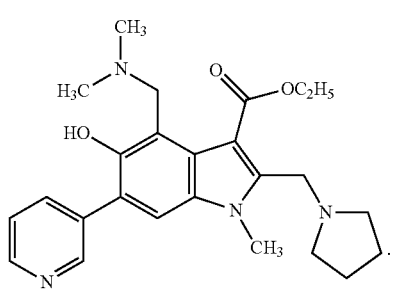

8. A pharmaceutical composition comprising the compound of claim 1 and a pharmaceutically acceptable excipient.

9. The pharmaceutical composition of claim 8 in the form of a tablet, capsule, or injection placed in pharmaceutically acceptable packing.

10. A method for the treatment of a viral disease in a human or warm-blooded animal comprising administering a compound of claim 1 to the human or warm-blooded animal in a pharmaceutically-effective dosage, wherein the viral disease is influenza or hepatitis.

11. The method of claim 10 wherein the viral disease is influenza.

12. The method of claim 10 wherein the viral disease is influenza A.

13. The method of claim 10 wherein the viral disease is infectious hepatitis.

14. The method of claim 10 wherein the viral disease is hepatitis C.

15. A therapeutic cocktail comprising a compound of claim 1 in combination with an anti-viral drug.

16. A method for the treatment of a viral disease in a human or warm-blooded animal comprising administering the cocktail of claim 15 to the human or warm-blooded animal in a pharmaceutically-effective dosage, wherein the viral disease is influenza or hepatitis.

17. The method of claim 16 wherein the viral disease is influenza.

18. The method of claim 16 wherein the viral disease is influenza A.

19. The method of claim 16 wherein the viral disease is infectious hepatitis.

20. The method of claim 16 wherein the viral disease is hepatitis C.

* * * * *